US012146187B2

(12) United States Patent
He et al.

(10) Patent No.: US 12,146,187 B2
(45) Date of Patent: Nov. 19, 2024

(54) METHODS OF TREATING DRY EYE DISEASE USING TNF ALPHA ANTAGONISTS

(71) Applicant: NOVARTIS AG, Basel (CH)

(72) Inventors: Yunsheng He, Waltham, MA (US);
Christian Leisner, Thalwil (CH);
Michael Wald, Acton, MA (US);
Georges Weissgerber, Marckolsheim (FR)

(73) Assignee: Novartis AG, Basel (CH)

( * ) Notice: Subject to any disclaimer, the term of this patent is extended or adjusted under 35 U.S.C. 154(b) by 194 days.

(21) Appl. No.: 16/311,001

(22) PCT Filed: Jun. 19, 2017

(86) PCT No.: PCT/IB2017/053625
§ 371 (c)(1),
(2) Date: Dec. 18, 2018

(87) PCT Pub. No.: WO2017/221128
PCT Pub. Date: Dec. 28, 2017

(65) Prior Publication Data
US 2019/0177407 A1    Jun. 13, 2019

Related U.S. Application Data

(60) Provisional application No. 62/352,091, filed on Jun. 20, 2016.

(51) Int. Cl.
*C12Q 1/68*    (2018.01)
*C12Q 1/6827*    (2018.01)
*C12Q 1/6858*    (2018.01)
*C12Q 1/6883*    (2018.01)
A61K 38/00    (2006.01)
A61P 27/02    (2006.01)
C07K 16/24    (2006.01)

(52) U.S. Cl.
CPC ......... *C12Q 1/6858* (2013.01); *C12Q 1/6827* (2013.01); *C12Q 1/6883* (2013.01); *A61K 38/00* (2013.01); *A61P 27/02* (2018.01); *C07K 16/241* (2013.01); *C07K 2317/56* (2013.01); *C07K 2317/622* (2013.01); *C07K 2317/76* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

2009/0098136 A1*   4/2009   Gamache ............ C07K 16/241
424/141.1

FOREIGN PATENT DOCUMENTS

WO    2009052140 A1    4/2009
WO    2012051734 A1    4/2012
WO    2013191352 A1    12/2013

OTHER PUBLICATIONS

Andiappan (BMC Genetics. 2010. 11: 36).*
Billiet (Gastroenterology, May 2013, vol. 144, abstract).*
Vehof et al; Invest Ophthalmol Vis Sci; 2014, vol. 55, pp. 7278-7283.*
Roach et al; Science; vol. 328, Apr. 30, 2010; pp. 636-639.*
Clinical Trial NCT02365519 (A Randomized, Double-masked, Vehicle-controlled Study of LME636 in the Relief of Persistent Ocular Discomfort in Subjects with Severe Dry Eye Disease; Feb. 19, 2015(Estimate)-Oct. 16, 2015) Year: 2015.*
Ji et al, "Neutralization of Ocular Surface TNF-[alpha] Reduces Ocular Surface and Lacrimal Gland Inflammation Induced by In Vivo Dry Eye", Investigative Opthalmology & Visual Science, vol. 54, No. 12, p. 7557, Nov. 15, 2014.
Gregory et al, "TNF receptor 1 genetic risk mirrors outcome of anti-TNF therapy in multiple sclerosis", Nature, vol. 488, No. 7412, pp. 508-511, Jul. 8, 2012.
International Preliminary Report on Patentability for International Patent Application No. PCT/IB2017/053625, dated Dec. 25, 2018.
Housley et al., "Genetics variants associated with autoimmunity drive NFkB signaling and responses to inflammatory stimuli," Sci Transl Med. Jun. 10, 2015; 7(291): 291ra93, pp. 1-10.
Ridder et al. "New drugs for the treatment of dry eye disease," Clinical Optometry, 2015, 91-102, 7.

* cited by examiner

*Primary Examiner* — Jehanne S Sitton
(74) *Attorney, Agent, or Firm* — Finnegan, Henderson, Farabow, Garrett & Dunner, LLP

(57) ABSTRACT

The disclosure is directed to novel predictive methods and personalized therapies for treating dry eye disease (DED). Specifically, this disclosure relates to methods of treating a patient having DED by selectively administering a TNFα antagonist, e.g., a TNFα antibody, such as LME636, to the patient on the basis of that patient being genetically predisposed to have a favorable response to treatment with the TNFα antagonist. Also disclosed herein are transmittable forms of information, diagnostic methods, and kits useful in predicting the likelihood that a patient having DED will respond to treatment with a TNFα antagonist, e.g., a TNFα antibody, such as LME636.

4 Claims, 5 Drawing Sheets

Specification includes a Sequence Listing.

SEQUENCE LISTING

```
<160> NUMBER OF SEQ ID NOS: 12

<210> SEQ ID NO 1
<211> LENGTH: 11
<212> TYPE: PRT
<213> ORGANISM: Artificial Sequence
<220> FEATURE:
<223> OTHER INFORMATION: synthetic peptide - Heavy chain CDR1

<400> SEQUENCE: 1

Gly Phe Thr Ile Ser Arg Ser Tyr Trp Ile Cys
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide - Heavy chain CDR2

<400> SEQUENCE: 2

Cys Ile Tyr Gly Asp Asn Asp Ile Thr Pro Leu Tyr Ala Asn Trp Ala
1               5                   10                  15

Lys Gly

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide - heavy chain CDR3

<400> SEQUENCE: 3

Leu Gly Tyr Ala Asp Tyr Ala Tyr Asp Leu
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic peptide - light chain CDR1

<400> SEQUENCE: 4

Gln Ser Ser Gln Ser Val Tyr Gly Asn Ile Trp Met Ala
1               5                   10

<210> SEQ ID NO 5
```

```
<211> LENGTH: 7
<212> TYPE: PRT
<213> ORGANISM: Artificial Sequence
<220> FEATURE:
<223> OTHER INFORMATION: Synthetic peptide - light chain CDR2

<400> SEQUENCE: 5

Gln Ala Ser Lys Leu Ala Ser
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide - light chain CDR3

<400> SEQUENCE: 6

Gln Gly Asn Phe Asn Thr Gly Asp Arg Tyr Ala
1               5                   10

<210> SEQ ID NO 7
<211> LENGTH: 112
<212> TYPE: PRT
<213> ORGANISM: Artificial Sequence
<220> FEATURE:
<223> OTHER INFORMATION: Synthetic peptide

<400> SEQUENCE: 7

Glu Ile Val Met Thr Gln Ser Pro Ser Thr Leu Ser Ala Ser Val Gly
1               5                   10                  15

Asp Arg Val Ile Ile Thr Cys Gln Ser Ser Gln Ser Val Tyr Gly Asn
            20                  25                  30

Ile Trp Met Ala Trp Tyr Gln Gln Lys Pro Gly Arg Ala Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Ala Glu Phe Thr Leu Thr Ile Ser Ser Leu
65                  70                  75                  80

Gln Pro Asp Asp Phe Ala Thr Tyr Tyr Cys Gln Gly Asn Phe Asn Thr
                85                  90                  95

Gly Asp Arg Tyr Ala Phe Gly Gly Thr Lys Leu Thr Val Leu Gly
            100                 105                 110

<210> SEQ ID NO 8
<211> LENGTH: 121
<212> TYPE: PRT
<213> ORGANISM: Artificial Sequence
<220> FEATURE:
<223> OTHER INFORMATION: Synthetic peptide

<400> SEQUENCE: 8

Glu Val Gln Leu Val Glu Ser Gly Gly Gly Ser Val Gln Pro Gly Gly
1               5                   10                  15

Ser Leu Arg Leu Ser Cys Thr Ala Ser Gly Phe Thr Ile Ser Arg Ser
            20                  25                  30

Tyr Trp Ile Cys Trp Val Arg Gln Ala Pro Gly Lys Gly Leu Glu Trp
        35                  40                  45

Val Gly Cys Ile Tyr Gly Asp Asn Asp Ile Thr Pro Leu Tyr Ala Asn
    50                  55                  60

Trp Ala Lys Gly Arg Phe Thr Ile Ser Arg Asp Thr Ser Lys Asn Thr
65                  70                  75                  80
```

```
Val Tyr Leu Gln Met Asn Ser Leu Arg Ala Glu Asp Thr Ala Thr Tyr
                85                  90                  95

Tyr Cys Ala Arg Leu Gly Tyr Ala Asp Tyr Ala Tyr Asp Leu Trp Gly
            100                 105                 110

Gln Gly Thr Thr Val Thr Val Ser Ser
        115                 120

<210> SEQ ID NO 9
<211> LENGTH: 253
<212> TYPE: PRT
<213> ORGANISM: Artificial Sequence
<220> FEATURE:
<223> OTHER INFORMATION: Synthetic peptide

<400> SEQUENCE: 9

Glu Ile Val Met Thr Gln Ser Pro Ser Thr Leu Ser Ala Ser Val Gly
1               5                   10                  15

Asp Arg Val Ile Ile Thr Cys Gln Ser Ser Gln Ser Val Tyr Gly Asn
            20                  25                  30

Ile Trp Met Ala Trp Tyr Gln Gln Lys Pro Gly Arg Ala Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Ala Glu Phe Thr Leu Thr Ile Ser Ser Leu
65                  70                  75                  80

Gln Pro Asp Asp Phe Ala Thr Tyr Tyr Cys Gln Gly Asn Phe Asn Thr
                85                  90                  95

Gly Asp Arg Tyr Ala Phe Gly Gln Gly Thr Lys Leu Thr Val Leu Gly
            100                 105                 110

Gly Gly Gly Gly Ser Gly Gly Gly Ser Gly Gly Gly Gly Ser Gly
        115                 120                 125

Gly Gly Gly Ser Glu Val Gln Leu Val Glu Ser Gly Gly Gly Ser Val
    130                 135                 140

Gln Pro Gly Gly Ser Leu Arg Leu Ser Cys Thr Ala Ser Gly Phe Thr
145                 150                 155                 160

Ile Ser Arg Ser Tyr Trp Ile Cys Trp Val Arg Gln Ala Pro Gly Lys
                165                 170                 175

Gly Leu Glu Trp Val Gly Cys Ile Tyr Gly Asp Asn Asp Ile Thr Pro
            180                 185                 190

Leu Tyr Ala Asn Trp Ala Lys Gly Arg Phe Thr Ile Ser Arg Asp Thr
        195                 200                 205

Ser Lys Asn Thr Val Tyr Leu Gln Met Asn Ser Leu Arg Ala Glu Asp
    210                 215                 220

Thr Ala Thr Tyr Tyr Cys Ala Arg Leu Gly Tyr Ala Asp Tyr Ala Tyr
225                 230                 235                 240

Asp Leu Trp Gly Gln Gly Thr Thr Val Thr Val Ser Ser
                245                 250

<210> SEQ ID NO 10
<211> LENGTH: 232
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (26)..(75)
<223> OTHER INFORMATION: CDR1 - X can be any naturally occurring amino
```

-continued

```
       acid.  at least three and up to 50 amino acids can be present
<220> FEATURE:
<221> NAME/KEY: MISC_FEATURE
<222> LOCATION: (90)..(139)
<223> OTHER INFORMATION: CDR2 - X can be any naturally occurring amino
       acid.  at least three and up to 50 amino acids can be present
<220> FEATURE:
<221> NAME/KEY: MISC_FEATURE
<222> LOCATION: (172)..(221)
<223> OTHER INFORMATION: CDR3 - X can be any naturally occurring amino
       acid.  at least three and up to 50 amino acids can be present

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Thr Ala Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Trp Val Arg Gln Ala
65                  70                  75                  80

Pro Gly Lys Gly Leu Glu Trp Val Gly Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Arg Phe Thr Ile Ser
    130                 135                 140

Arg Asp Thr Ser Lys Asn Thr Val Tyr Leu Gln Met Asn Ser Leu Arg
145                 150                 155                 160

Ala Glu Asp Thr Ala Val Tyr Tyr Cys Ala Arg Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Trp Gly Gln
    210                 215                 220

Gly Thr Leu Val Thr Val Ser Ser
225                 230

<210> SEQ ID NO 11
<211> LENGTH: 231
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (24)..(73)
<223> OTHER INFORMATION: CDR1 - X can be any naturally occurring amino
       acid.  at least three and up to 50 amino acids can be presen
<220> FEATURE:
<221> NAME/KEY: MISC_FEATURE
<222> LOCATION: (89)..(138)
<223> OTHER INFORMATION: CDR2 - X can be any naturally occurring amino
       acid.  at least three and up to 50 amino acids can be presen
<220> FEATURE:
<221> NAME/KEY: MISC_FEATURE
<222> LOCATION: (171)..(220)
```

<223> OTHER INFORMATION: CDR3 - X can be any naturally occurring amino
      acid. at least three and up to 50 amino acids can be presen

<400> SEQUENCE: 11

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Gly Val Pro Ser Arg Phe
    130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Phe Gly Gln Gly
    210                 215                 220

Thr Lys Leu Thr Val Leu Gly
225                 230

<210> SEQ ID NO 12
<211> LENGTH: 254
<212> TYPE: PRT
<213> ORGANISM: Artificial Sequence
<220> FEATURE:
<223> OTHER INFORMATION: Synthetic peptide

<400> SEQUENCE: 12

Met Glu Ile Val Met Thr Gln Ser Pro Ser Thr Leu Ser Ala Ser Val
1               5                   10                  15

Gly Asp Arg Val Ile Ile Thr Cys Gln Ser Ser Gln Ser Val Tyr Gly
            20                  25                  30

Asn Ile Trp Met Ala Trp Tyr Gln Gln Lys Pro Gly Arg Ala Pro Lys
        35                  40                  45

Leu Leu Ile Tyr Gln Ala Ser Lys Leu Ala Ser Gly Val Pro Ser Arg
    50                  55                  60

Phe Ser Gly Ser Gly Ser Gly Ala Glu Phe Thr Leu Thr Ile Ser Ser
65                  70                  75                  80

Leu Gln Pro Asp Asp Phe Ala Thr Tyr Tyr Cys Gln Gly Asn Phe Asn
                85                  90                  95

Thr Gly Asp Arg Tyr Ala Phe Gly Gln Gly Thr Lys Leu Thr Val Leu

-continued

```
                100                 105                 110
Gly Gly Gly Gly Gly Ser Gly Gly Gly Ser Gly Gly Gly Gly Ser
            115                 120                 125

Gly Gly Gly Gly Ser Glu Val Gln Leu Val Glu Ser Gly Gly Gly Ser
            130             135                 140

Val Gln Pro Gly Gly Ser Leu Arg Leu Ser Cys Thr Ala Ser Gly Phe
145                 150                 155                 160

Thr Ile Ser Arg Ser Tyr Trp Ile Cys Trp Val Arg Gln Ala Pro Gly
                165                 170                 175

Lys Gly Leu Glu Trp Val Gly Cys Ile Tyr Gly Asp Asn Asp Ile Thr
                180                 185                 190

Pro Leu Tyr Ala Asn Trp Ala Lys Gly Arg Phe Thr Ile Ser Arg Asp
            195                 200                 205

Thr Ser Lys Asn Thr Val Tyr Leu Gln Met Asn Ser Leu Arg Ala Glu
            210                 215                 220

Asp Thr Ala Thr Tyr Tyr Cys Ala Arg Leu Gly Tyr Ala Asp Tyr Ala
225                 230                 235                 240

Tyr Asp Leu Trp Gly Gln Gly Thr Thr Val Thr Val Ser Ser
                245                 250
```

METHODS OF TREATING DRY EYE DISEASE USING TNF ALPHA ANTAGONISTS

TECHNICAL FIELD

The disclosure is directed to predictive methods, personalized therapies, kits, transmittable forms of information and methods for treating patients having dry eye disease.

BACKGROUND OF THE DISCLOSURE

Dry eye disease (DED) is a common and multifactorial disease of the tears and ocular surface characterized by ocular surface inflammation and increased osmolarity of the tear film that result in symptoms of discomfort, visual disturbance and tear film instability (Lienert J P, Tarko L, Uchino M, Christen W G, Schaumberg D A. (2016). Long-term Natural History of Dry Eye Disease from the Patient's Perspective. Ophthalmology. 123(2):425-33). The only available pharmacological treatment is topical cyclosporine that is an anti-inflammatory agent and approved for increasing tear production. Steroids are also used to treat DED but contraindicated for long-term use because of side effects. For more severe forms of DED, serum tears and scleral contact lenses are recommended. However, none of these treatments fully addresses the underlying causes of DED (Marshall L L, Roach J M. (2016). Treatment of Dry Eye Disease. Consult Pharm. 2016; 31(2):96-106).

Dry eye, also referred to as keratoconjunctivitis sicca, is a common ophthalmological disorder affecting millions of persons each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjögren's syndrome and cicatricial pemphigoid, may also lead to dry eye conditions. Transient symptoms of dry eye associated with refractive surgery have been reported to last in some cases from six weeks to six months or more following surgery.

Although it appears that dry eye may result from a number of unrelated pathogenic causes, all presentations of the complication share a common effect, that is the breakdown of the pre-ocular tear film, which results in exposure of the ocular surface, dehydration, and cytokine production resulting in many of the symptoms outlined above (Lemp, Report of the National Eye Institute/Industry Workshop on Clinical Trials in Dry Eyes, The CLAO Journal, volume 21, number 4, pages 221-231 (1995)).

Practitioners have taken several approaches to the treatment of dry eye. One common approach has been to supplement and stabilize the ocular tear film using so-called artificial tears instilled throughout the day. Other approaches include the use of ocular inserts that promote retention of tears (e.g., punctal plugs) or the stimulation of endogenous tear production.

Examples of the tear substitution approach include the use of buffered, isotonic saline solutions, aqueous solutions containing water soluble polymers that render the solutions more viscous and thus less easily shed by the eye. Tear film stabilization is also attempted by providing one or more components of the tear film such as phospholipids and oils. Phospholipid compositions have been shown to be useful in treating dry eye; see, e.g., McCulley and Shine, Tear film structure and dry eye, Contactologia, volume 20(4), pages 145-49 (1998); and Shine and McCulley, Keratoconjunctivitis sicca associated with meibomian secretion polar lipid abnormality, Archives of Ophthalmology, volume 116(7), pages 849-52 (1998).

Another approach involves the provision of lubricating substances in lieu of artificial tears. For example, U.S. Pat. No. 4,818,537 (Guo) discloses the use of a lubricating, liposome-based composition, and U.S. Pat. No. 5,800,807 (Hu et al.) discloses compositions containing glycerin and propylene glycol for treating dry eye.

Although these approaches have met with some success, problems in the treatment of dry eye nevertheless remain, since the use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive.

Aside from efforts described above, which are directed primarily to the palliative alleviation of symptoms associated with dry eye, methods and compositions directed to treatment of the physiological conditions that cause such symptoms have also been pursued. For example, U.S. Pat. No. 5,041,434 (Lubkin) discloses the use of sex steroids, such as conjugated estrogens, to treat dry eye conditions in post-menopausal women; U.S. Pat. No. 5,290,572 (MacKeen) discloses the use of finely divided calcium ion compositions to stimulate pre-ocular tear film production.

Such efforts to treat the underlying causes of dry eye have focused on treating inflammation of the relevant ocular tissues and meibomian gland dysfunction. The use of various types of agents for such treatment of dry eye patients has been disclosed, including steroids (e.g., U.S. Pat. No. 5,958,912; Marsh et al., Topical nonpreserved methylprednisolone therapy for keratoconjunctivitis sicca in Sjögren's syndrome, Ophthalmology, 106(4): 811-816 (1999); and Pflugfelder et al., U.S. Pat. No. 6,153,607), cytokine release inhibitors (Yanni, J. M.; et. al. WO 00/03705 A1), cyclosporine A (Tauber, J. Adv. Exp. Med. Biol. 1998, 438 (Lacrimal Gland, Tear Film, and Dry Eye Syndromes 2), 969), and mucosecretatogues, such as 15-HETE (Yanni et. al., U.S. Pat. No. 5,696,166).

Elevation of inflammatory cytokines, including tumor necrosis factor α (TNF-α), in affected tissues has been reported in many studies (Massingale M L, Li X, Vallabhajosyula M, Chen D, Wei Y, et al. (2009). Analysis of inflammatory cytokines in the tears of dry eye patients. Cornea. 28(9):1023-7; Chen Y, Zhang X, Yang L, Li M, Li B, et al. (2014). Decreased PPAR-γ expression in the conjunctiva and increased expression of TNF-α and IL-1β in the conjunctiva and tear fluid of dry eye mice. Mol Med Rep. 9(5):2015-23). A correlation between TNFα levels in tears or conjunctival tissue and clinical severity of DED was also observed (Lee S Y, Han S J, Nam S M, Yoon S C, Ahn J M, et al. (2013). Analysis of tear cytokines and clinical correlations in Sjögren syndrome dry eye patients and non-Sjögren syndrome dry eye patients. Am J Ophthalmol. 156(2):247-253). TNF-α is a pleiotropic cytokine and involved in regulation of cell trafficking, activation, and host defenses against various pathogens upon binding to its receptors. Anti-TNF agents have demonstrated clinical efficacy in treating human autoimmune diseases including rheumatoid arthritis and Crohn's disease. However, topical anti-TNF therapy for DED has not been evaluated despite evidence of TNF-α involvement in DED (Ji Y W, Byun Y J, Choi W, Jeong E, Kim J S, et al. (2013). Neutralization of ocular surface TNF-α reduces ocular surface and lacrimal gland inflammation induced by in vivo dry eye. Invest Ophthalmol Vis Sci. 54(12):7557-66).

A recent study by Hallak et al. showed that Val66Met in the brain-derived neurotrophic factor (BDNF) gene and two SNPs, Fok1 and Apa1, in the vitamin D receptor (VDR) gene may potentially be associated with DED (Hallak et al., Investigative Ophthalmology & Visual Science September 2015, Vol. 56, 5990-5996). However, there is no known SNP that can identify DED patients most likely to benefit from TNFα antagonism.

BRIEF SUMMARY OF THE DISCLOSURE

Provided herein are novel predictive methods and personalized therapies for patients having dry eye disease (DED) that maximize the benefit and minimize the risk of TNFα antagonism in these populations by identifying those patients likely to respond favorably prior to treatment with a TNFα antagonist. This finding is based, in part, on the determinations that DED patients carrying DED response marker selected from an rs1800693 response allele display improved response to LME636 relative to DED patients that do not carry the allele.

We thus contemplate that testing subjects for the presence of an rs1800693 response allele will be useful in a variety of pharmaceutical products and methods that involve identifying DED patients who are more likely to respond to TNFα antagonsim and in helping physicians decide whether to prescribe TNFα antagonists (e.g., LME636) to those patients or whether to prescribe an alternative therapeutic regimen.

Accordingly, it is one object of the disclosure to provide methods of treating a patient having DED by administering the patient a therapeutically effective amount of a TNFα antagonist, e.g., a TNFα antibody, such as LME636, based on certain aspects of the patient's biochemical profile. It is another object of the disclosure to provide methods of identifying a patient having DED who is more likely to respond to treatment with a TNFα antagonist, e.g., a TNFα antibody, such as LME636, based on certain aspects of the patient's biochemical profile. It is another object of the disclosure to provide methods of determining the likelihood that a patient having DED will respond to treatment with a TNFα antagonist, e.g., a TNFα antibody, such as LME636, based on certain aspects of the patient's biochemical profile.

Disclosed herein are various methods of selectively treating a patient having DED. In some embodiments, these methods comprise assaying a biological sample from the patient for the disclosed DED response marker; and thereafter selectively administering a therapeutically effective amount of a TNFα antagonist, e.g., a TNFα antibody, such as LME636, to the patient if the patient has the response marker.

Disclosed herein are also various methods of predicting the likelihood that a patient having DED will respond to treatment with a TNFα antagonist, e.g., a TNFα antibody, such as LME636. In some embodiments, these methods comprise detecting the disclosed DED response markers in a biological sample from the patient, wherein the presence of the response marker is indicative of an increased likelihood that the patient will respond to treatment with the TNFα antagonist.

In preferred embodiments, the TNFα antagonist is a TNFα binding molecule, preferably an antibody or antigen-binding portion thereof, most preferably LME636. In some embodiments, the DED response marker is at least one DED response marker as shown in Table 1.

Additional methods, uses, and kits are provided in the following description and appended claims. Further features, advantages and aspects of the present disclosure will become apparent to those skilled in the art from the following description and appended claims.

DETAILED DESCRIPTION OF THE DISCLOSURE

Figure 1:
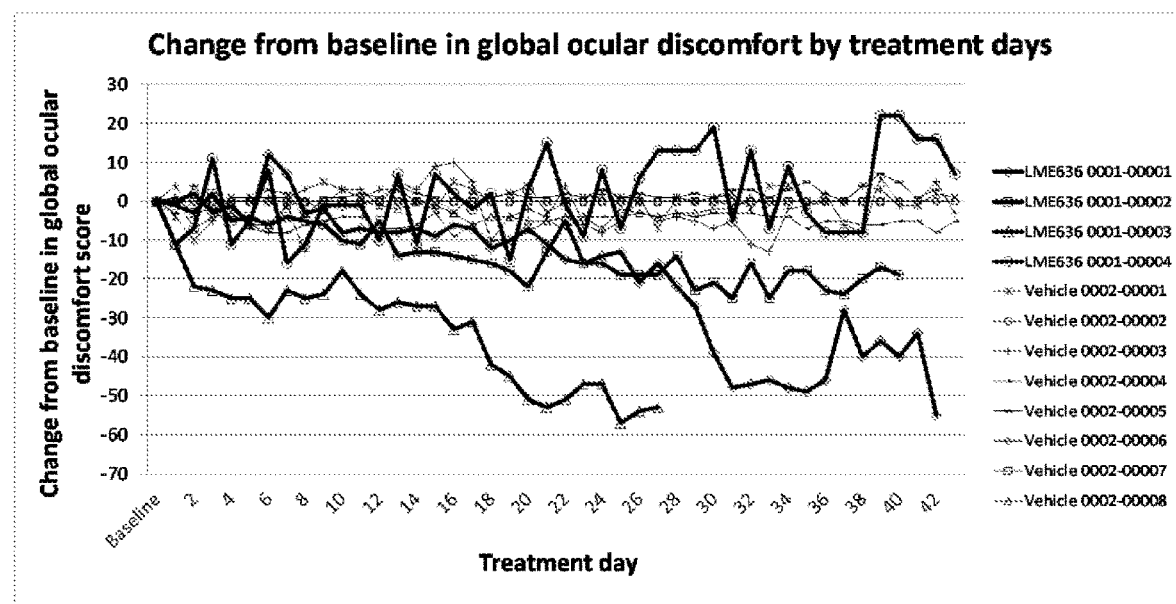
FIG. 1 illustrates the symptomatic changes for twelve patients having the rs1800693 CC genotype, 4 patients treated with LME636 and 8 treated with vehicle, from baseline to day 43.
Figure 2:
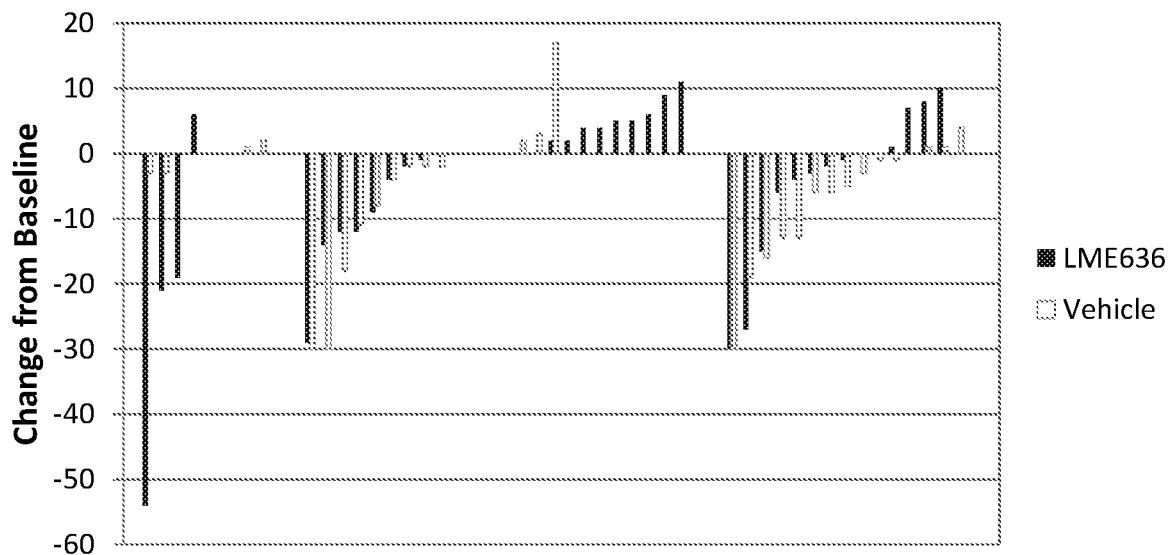
FIG. 2 is a waterfall plot showing change from baseline in global ocular discomfort score at day 26 for all patients treated with LME636 or vehicle to allow visualization of the symptomatic changes by treatment and rs1800693 genotype.
Figure 3:
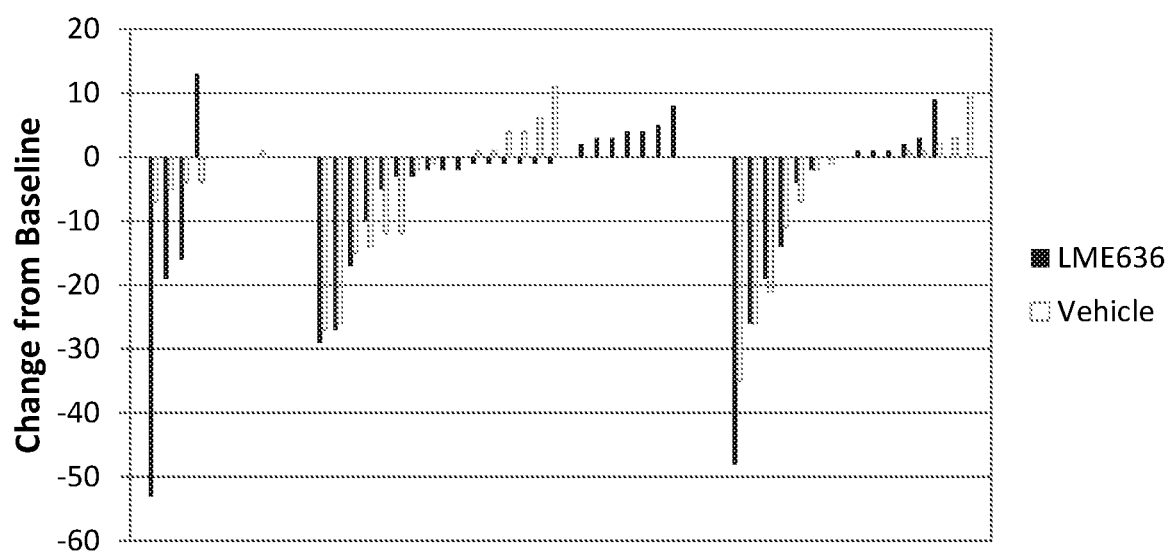
FIG. 3 is a waterfall plot showing change from baseline in global ocular discomfort score at day 27 for all patients treated with LME636 or vehicle to allow visualization of the symptomatic changes by treatment and rs1800693 genotype.
Figure 4:
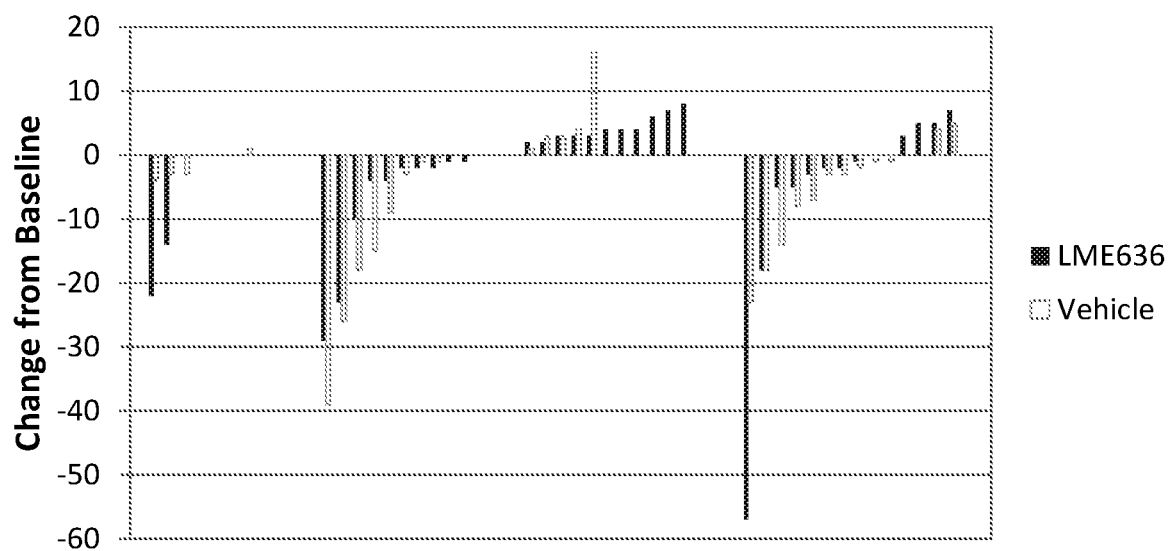
FIG. 4 is a waterfall plot showing change from baseline in global ocular discomfort score at day 28 for all patients treated with LME636 or vehicle to allow visualization of the symptomatic changes by treatment and rs1800693 genotype.
Figure 5:
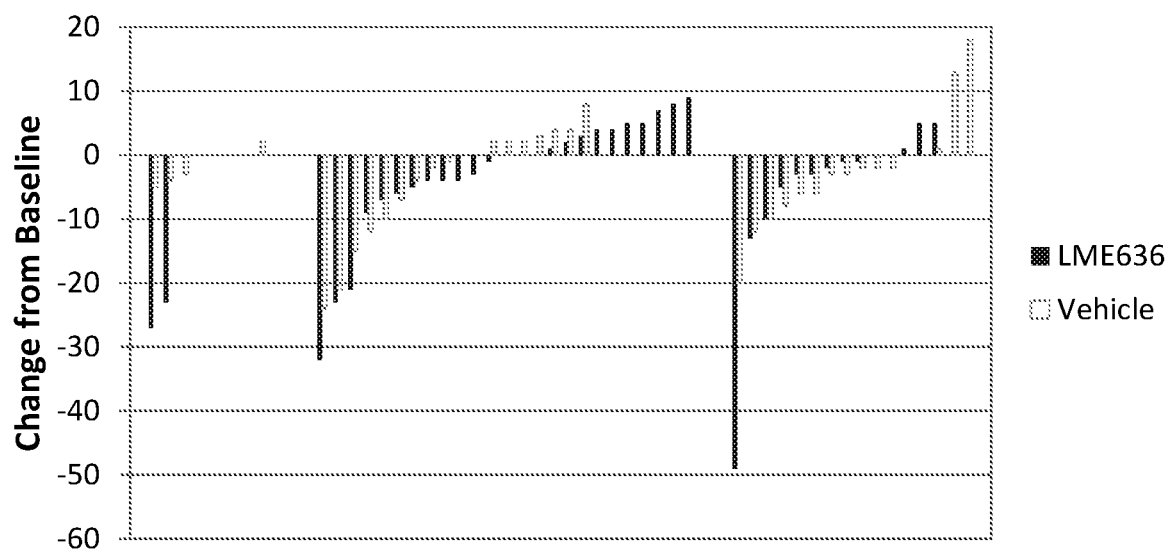
FIG. 5 is a waterfall plot showing change from baseline in global ocular discomfort score at day 29 for all patients treated with LME636 or vehicle to allow visualization of the symptomatic changes by treatment and rs1800693 genotype.

The term "comprising" encompasses "including" as well as "consisting," e.g. a composition "comprising" X may consist exclusively of X or may include something additional, e.g., X+Y.

The term "about" in relation to a numerical value x means+/−10% unless the context dictates otherwise.

As used herein, the terms "subject" and "patient" include any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

The term "assaying" is used to refer to the act of identifying, screening, probing, testing measuring or determining, which act may be performed by any conventional means. For example, a sample may be assayed for the presence of a particular genetic or protein marker by using an ELISA assay, a Northern blot, imaging, serotyping, cellular typing, gene sequencing, phenotyping, haplotyping, immunohistochemistry, western blot, mass spectrometry, etc. The term "detecting" (and the like) means the act of extracting particular information from a given source, which may be direct or indirect. In some embodiments of the predictive methods disclosed herein, the presence of a given thing (e.g., allele, level of protein, etc.) is detected in a biological sample indirectly, e.g., by querying a database. The terms "assaying" and "determining" contemplate a transformation of matter, e.g., a transformation of a biological sample, e.g., a blood sample or other tissue sample, from one state to another by means of subjecting that sample to physical testing.

The term "obtaining" means to procure, e.g., to acquire possession of in any way, e.g., by physical intervention (e.g., biopsy, blood draw) or non-physical intervention (e.g., transmittal of information via a server), etc.

The phrase "assaying a biological sample . . . " and the like, is used to mean that a sample may be tested (either directly or indirectly) for either the presence of a given DED response marker. It will be understood that, in a situation where the presence of a substance denotes one probability and the absence of a substance denotes a different probabiltity, then either the presence or the absence of such substance may be used to guide a therapeutic decision. For example, one may determine if a patient has DED response marker by determining the actual existence of particular response allele in the patient or by determining the absence of the particular response allele in the patient. In both such cases, one has determined whether the patient has the presence of the DED response marker. The disclosed methods involve, inter alia, determining whether a particular individual has a DED response marker. This determination is undertaken by identifying whether the patient has a DED response marker in Table 1. Each of these determinations (i.e., presence or absence), on its own, provides the allelic status of the patient and thus each of these determinations equally provide an indication of whether a particular individual would or would not respond more favorably to TNFα antagonism.

TABLE 1

| Gene | SNP | Location | Response Allele (copies for response) |
| --- | --- | --- | --- |
| TNFR1 | rs1800693 | Intronic | C (One or two) |
| TNFR1 | rs1800693 | Intronic | T (One or two) |

Table 1 shows the various response alleles of the disclosure. Column 1 provides the gene in which the SNP of column 2 resides, and column 3 provides the general location of that SNP in that gene.

While the SNP listed in Table 1 has predictive value for TNFα antagonism if there is any of the given response alleles (i.e., the patient is either homozygous or heterozygous for the given response allele), as discussed in the Examples below, patients with the CC genotype tended to have a larger improvement to LME636 than those with the CT or TT genotypes in response to LME636.

The term "dry eye," also known as conjunctivitis sicca or keratoconjunctivitis sicca, is a common ophthalmological disorder involving breakdown of the pre-ocular tear film, resulting in dehydration of the exposed outer surface of the eye. In certain embodiments, the "dry eye" is characterized as moderate to severe, severity being determined by one of skill in the art, for example based on global ocular discomfort score as described herein. Methods for determining severity of dry eye are also described, for example, in the DEWS definition and classification guidelines from the 2007 International Dry Eye Workshop (see "The Ocular Surface" April 2007, Vol. 5, No. 2, pages 75-92) or the methods described by Sullivan et al. (Investigative Ophthalmology & Visual Science, December 2010, Vol. 51, pg. 6125-6130).

The term "TNFα" refers to tumour necrosis factor alpha (also known as cachectin), which is a naturally occurring mammalian cytokine produced by numerous cell types, including monocytes and macrophages in response to endotoxin or other stimuli. TNFα is a major mediator of inflammatory, immunological, and pathophysiological reactions (Grell, M., et al. (1995) Cell, 83: 793-802). "TNFα" includes wild-type TNFα from various species (e.g., human, mouse, and monkey), polymorphic variants of TNFα, and functional equivalents of TNFα. Functional equivalents of TNFα according to the present disclosure preferably have at least about 85%, 95%, 96%, 97%, 98%, or even 99% overall sequence identity with a wild-type TNFα (e.g., human TNFα), and substantially retain the ability to mediate inflammatory, immunological, and pathophysiological reactions.

"TNFα antagonist" as used herein refers to a molecule capable of antagonizing (e.g., reducing, inhibiting, decreasing, delaying) TNFα function, expression and/or signalling (e.g., by blocking the binding of TNFα to the TNFα receptor). Non-limiting examples of TNFα antagonists include TNFα binding molecules and TNFα receptor binding molecules. In some embodiments of the disclosed methods, regimens, kits, processes, uses and compositions, an TNFα antagonist is employed.

By "TNFα binding molecule" is meant any molecule capable of binding to the human TNFα antigen either alone or associated with other molecules. The binding reaction may be shown by standard methods (qualitative assays) including, for example, a binding assay, competition assay or a bioassay for determining the inhibition of TNFα binding to its receptor or any kind of binding assays, with reference to a negative control test in which an antibody of unrelated specificity, but ideally of the same isotype, e.g., an anti-CD25 antibody, is used. Non-limiting examples of TNFα binding molecules include small molecules, TNFα receptor decoys, and antibodies that bind to TNFα as produced by B-cells or hybridomas and chimeric, CDR-grafted or human antibodies or any fragment thereof, e.g., F(ab')$_2$ and Fab fragments, as well as single chain or single domain antibodies. Preferably the TNFα binding molecule antagonizes (e.g., reduces, inhibits, decreases, delays) TNFα function, expression and/or signalling. In some embodiments of the disclosed methods, regimens, kits, processes, uses and compositions, an TNFα binding molecule is employed.

By "TNFα receptor binding molecule" is meant any molecule capable of binding to the human TNFα receptor either alone or associated with other molecules. The binding reaction may be shown by standard methods (qualitative assays) including, for example, a binding assay, competition assay or a bioassay for determining the inhibition of TNFα receptor binding to TNFα or any kind of binding assays, with reference to a negative control test in which an antibody of unrelated specificity, but ideally of the same isotype is used. Non-limiting examples of TNFα receptor binding molecules include small molecules, TNFα decoys, and antibodies to the TNFα receptor as produced by B-cells or hybridomas and chimeric, CDR-grafted or human antibodies or any fragment thereof, e.g., F(ab')$_2$ and Fab fragments, as well as single chain or single domain antibodies. Preferably the TNFα receptor binding molecule antagonizes (e.g., reduces, inhibits, decreases, delays) TNFα function, expression and/or signalling. In some embodiments of the disclosed methods, regimens, kits, processes, uses and compositions, a TNFα receptor binding molecule is employed.

The term "antibody" as referred to herein includes whole antibodies and any antigen-binding portion or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as V$_H$) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The $V_H$ and $V_L$ regions can be further subdivided into regions of hypervariability, termed hypervariable regions or complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. In some embodiments of the disclosed methods, regimens, kits, processes, uses and compositions, an antibody to TNFα or the TNFα receptor is employed, preferably an antibody to TNFα, e.g., LME636.

The term "antigen-binding portion" of an antibody as used herein, refers to fragments of an antibody that retain the ability to specifically bind to an antigen (e.g., TNFα). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, CL and CH1 domains; a F(ab)2 fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated CDR. Exemplary antigen binding sites include the CDRs of LME636 as set forth in SEQ ID NOs:1-6 (Table 2), preferably the heavy chain CDR3. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies are also intended to be encompassed within the term "antibody". Single chain antibodies and antigen-binding portions are obtained using conventional techniques known to those of skill in the art. In some embodiments of the disclosed methods, regimens, kits, processes, uses and compositions, a single chain antibody or an antigen-binding portion of an antibody against TNFα (e.g., LME636) or the TNFα receptor is employed.

An "isolated antibody", as used herein, refers to an antibody that is substantially free of other antibodies having different antigenic specificities (e.g., an isolated antibody that specifically binds TNFα is substantially free of antibodies that specifically bind antigens other than TNFα). The term "monoclonal antibody" or "monoclonal antibody composition" as used herein refer to a preparation of antibody molecules of single molecular composition. The term "human antibody", as used herein, is intended to include antibodies having variable regions in which both the framework and CDR regions are derived from sequences of human origin. A "human antibody" need not be produced by a human, human tissue or human cell. The human antibodies of the disclosure may include amino acid residues not encoded by human sequences (e.g., mutations introduced by random or site-specific mutagenesis in vitro, by N-nucleotide addition at junctions in vivo during recombination of antibody genes, or by somatic mutation in vivo). In some embodiments of the disclosed methods, regimens, kits, processes, uses and compositions, the TNFα antagonist is a human antibody, an isolated antibody, and/or a monoclonal antibody. In other embodiments of the disclosed methods, regimens, kits, processes, uses and compositions, the TNFα antagonist is a recombinant single-chain (scFv) antibody.

The term "$K_D$" is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. Methods for determining the $K_D$ of an antibody are known in the art, for instance using a biosensor system such as a Biacore® system. In some embodiments, the TNFα antagonist, e.g., TNFα binding molecule (e.g., TNFα antibody or antigen-binding portion thereof, e.g., LME636) or TNFα receptor binding molecule (e.g., TNFα receptor antibody or antigen-binding portion thereof) binds human TNFα with a $K_D$ of about 5-250 pM.

The term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. Standard assays to evaluate the binding affinity of the antibodies toward TNFα of various species are known in the art, including for example, ELISAs, western blots and RIAs. The binding kinetics (e.g., binding affinity) of the antibodies also can be assessed by standard assays known in the art, such as by Biacore analysis.

An antibody that "inhibits" one or more of these TNFα functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (or when a control antibody of irrelevant specificity is present). An antibody that inhibits TNFα activity affects a statistically significant decrease, e.g., by at least about 10% of the measured parameter, by at least 50%, 80% or 90%, and in certain embodiments of the disclosed methods, uses, processes, kits and compositions, the TNFα antibody used may inhibit greater than 95%, 98% or 99% of TNFα functional activity.

The term "derivative", unless otherwise indicated, is used to define amino acid sequence variants, and covalent modifications (e.g., pegylation, deamidation, hydroxylation, phosphorylation, methylation, etc.) of an TNFα antagonist, e.g., TNFα binding molecule (e.g., TNFα antibody or antigen-binding portion thereof, e.g., LME636) or TNFα receptor binding molecule (e.g., TNFα receptor antibody or antigen-binding portion thereof) according to the present disclosure, e.g., of a specified sequence (e.g., a variable domain). A "functional derivative" includes a molecule having a qualitative biological activity in common with the disclosed TNFα antagonists, e.g., TNFα binding molecules. A functional derivative includes fragments and peptide analogs of a TNFα antagonist as disclosed herein. Fragments comprise regions within the sequence of a polypeptide according to the present disclosure, e.g., of a specified sequence. Functional derivatives of the TNFα antagonists disclosed herein (e.g., functional derivatives of LME636) preferably comprise $V_H$ and/or $V_L$ domains that have at least about 65%, 75%, 85%, 95%, 96%, 97%, 98%, or even 99% overall sequence identity with the $V_H$ and/or $V_L$ sequences of the TNFα binding molecules disclosed herein (e.g., the $V_H$ and/or $V_L$ sequences of Table 2), and substantially retain the ability to bind human TNFα.

The phrase "substantially identical" means that the relevant amino acid or nucleotide sequence (e.g., $V_H$ or $V_L$ domain) will be identical to or have insubstantial differences (e.g., through conserved amino acid substitutions) in comparison to a particular reference sequence. Insubstantial differences include minor amino acid changes, such as 1 or 2 substitutions (e.g., conservative substitutions, such as swapping a serine for a threonine, or substitutions at positions not involved in antibody activity, structural integrity, complement fixation, etc.) in a 5 amino acid sequence of a specified region (e.g., $V_H$ or $V_L$ domain). In the case of antibodies, the second antibody has the same specificity and has at least 50% of the affinity of the same. Sequences substantially identical (e.g., at least about 85% sequence identity) to the sequences disclosed herein are also part of this disclosure. In some embodiments, the sequence identity of a derivative TNFα antibody (e.g., a derivative of LME636, e.g., an LME636 biosimilar antibody) can be about 90% or greater, e.g., 90%, 91%, 92%, 93%, 94%, 95%, 96%, 97%, 98%, 99% or higher relative to the disclosed sequences.

"Identity" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent identity, and not considering any conservative substitutions as part of the sequence identity. Neither N- or C-terminal extensions nor insertions shall be construed as reducing identity. Methods and computer programs for the alignment are well known. The percent identity can be determined by standard alignment algorithms, for example, the Basic Local Alignment Search Tool (BLAST) described by Altshul et al. ((1990) J. Mol. Biol., 215: 403 410); the algorithm of Needleman et al. ((1970) J. Mol. Biol., 48: 444 453); or the algorithm of Meyers et al. ((1988) Comput. Appl. Biosci., 4: 11 17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

"Amino acid(s)" refer to all naturally occurring L-α-amino acids, e.g., and include D-amino acids. The phrase "amino acid sequence variant" refers to molecules with some differences in their amino acid sequences as compared to the sequences according to the present disclosure. Amino acid sequence variants of a polypeptide according to the present disclosure, e.g., of a specified sequence, still have the ability to bind the human TNFα. Amino acid sequence variants include substitutional variants (those that have at least one amino acid residue removed and a different amino acid inserted in its place at the same position in a polypeptide according to the present disclosure), insertional variants (those with one or more amino acids inserted immediately adjacent to an amino acid at a particular position in a polypeptide according to the present disclosure) and deletional variants (those with one or more amino acids removed in a polypeptide according to the present disclosure).

The term "pharmaceutically acceptable" means a non-toxic material that does not interfere with the effectiveness of the biological activity of the active ingredient(s).

The term "administering" in relation to a compound, e.g., an TNFα binding molecule or another agent, is used to refer to delivery of that compound to a patient by any route.

As used herein, a "therapeutically effective amount" refers to an amount of an TNFα antagonist, e.g., TNFα binding molecule (e.g., TNFα antibody or antigen-binding portion thereof, e.g., LME636) or TNFα receptor binding molecule (e.g., TNFα receptor antibody or antigen-binding portion thereof) that is effective, upon single or multiple dose administration to a patient (such as a human) for treating, preventing, preventing the onset of, curing, delaying, reducing the severity of, ameliorating at least one symptom of a disorder or recurring disorder, or prolonging the survival of the patient beyond that expected in the absence of such treatment. When applied to an individual active ingredient (e.g., a TNFα antagonist, e.g., LME636) administered alone, the term refers to that ingredient alone. When applied to a combination, the term refers to combined amounts of the active ingredients that result in the therapeutic effect, whether administered in combination, serially or simultaneously.

The term "treatment" or "treat" refer to both prophylactic or preventative treatment (as the case may be) as well as curative or disease modifying treatment, including treatment of a patient at risk of contracting the disease or suspected to have contracted the disease as well as patients who are ill or have been diagnosed as suffering from a disease or medical condition, and includes suppression of clinical relapse. The treatment may be administered to a patient having a medical disorder or who ultimately may acquire the disorder, in order to prevent, cure, delay the onset of, reduce the severity of, or ameliorate one or more symptoms of a disorder or recurring disorder, or in order to prolong the survival of a patient beyond that expected in the absence of such treatment.

The phrase "respond to treatment" is used to mean that a patient, upon being delivered a particular treatment, e.g., a TNFα binding molecule (e.g., LME636) shows a clinically meaningful benefit from said treatment. In the case of DED, such criteria include, e.g., an improvement in global ocular discomfort score. All such criteria are acceptable measures of whether a patient is responding to a given treatment. The phrase "respond to treatment" is meant to be construed comparatively, rather than as an absolute response. For example, a DED patient having an DED response marker is predicted to have more benefit from treatment with a TNFα antagonist than a DED patient who does not have the DED response marker. These carriers of DED response markers respond more favorably to treatment with the TNFα antagonist, and may simply be said to "respond to treatment" with a TNFα antagonist.

The phrase "receiving data" is used to mean obtaining possession of information by any available means, e.g., orally, electronically (e.g., by electronic mail, encoded on diskette or other media), written, etc.

As used herein, "selecting" and "selected" in reference to a patient is used to mean that a particular patient is specifically chosen from a larger group of patients on the basis of (due to) the particular patient having a predetermined criteria, e.g., the patient has a DED response marker. Similarly, "selectively treating" refers to providing treatment to a patient having DED, where that patient is specifically chosen from a larger group of patients on the basis of the particular patient having predetermined criteria, e.g., a DED patient specifically chosen for treatment due to the patient having a DED response marker. Similarly, "selectively administering" refers to administering a drug to a patient that is specifically chosen from a larger group of patients on the basis of (due to) the particular patient having predetermined criteria, e.g., a particular genetic or other biological marker. By selecting, selectively treating and selectively administering, it is meant that a patient is delivered a personalized therapy based on the patient's particular biology, rather than being delivered a standard treatment regimen based solely on the patient having DED. Selecting, in reference to a method of treatment as used herein, does not refer to fortuitous treatment of a patient that has a DED response marker, but rather refers to the deliberate choice to administer a TNFα antagonist to a patient based on the patient having a DEDI response marker. Thus, selective treatment differs from standard treatment, which delivers a particular drug to all patients, regardless of their allelic status.

As used herein, "predicting" indicates that the methods described herein provide information to enable a health care provider to determine the likelihood that an individual having DED will respond to or will respond more favorably to treatment with a TNFα binding molecule. It does not refer to the ability to predict response with 100% accuracy. Instead, the skilled artisan will understand that it refers to an increased probability.

As used herein, "likelihood" and "likely" is a measurement of how probable an event is to occur. It may be used interchangably with "probability". Likelihood refers to a probability that is more than speculation, but less than certainty. Thus, an event is likely if a reasonable person using common sense, training or experience concludes that, given the circumstances, an event is probable. In some embodiments, once likelihood has been ascertained, the patient may be treated (or treatment continued, or treatment proceed with a dosage increase) with the TNFα binding molecule or the patient may not be treated (or treatment discontinued, or treatment proceed with a lowered dose) with the TNFα binding molecule.

The phrase "increased likelihood" refers to an increase in the probability that an event will occur. For example, some methods herein allow prediction of whether a patient will display an increased likelihood of responding to treatment with an TNFα binding molecule or an increased likelihood of responding better to treatment with a TNFα binding molecule in comparison to a patient having DED who does not have a DED response marker.

As used herein "SNP" refers to "single nucleotide polymorphism". A single nucleotide polymorphism is a DNA sequence variation occurring when a single nucleotide in the genome (or other shared sequence) differs between members of a biological species or paired chromosomes in an individual. Most SNPs have only two alleles, and one is usually more common in the population. A SNP may be present in an exon or an intron of a gene, an upstream or downstream untranslated region of a gene, or in a purely genomic location (i.e., non-transcribed). When a SNP occurs in the coding region of a gene, the SNP may be silent (i.e., a synonymous polymorphism) due to the redundancy of the genetic code, or the SNP may result in a change in the sequence of the encoded polypeptide (i.e., a non-synonymous polymorphism). In the instant disclosure, SNPs are identified by their Single Nucleotide Polymorphism Database (dbSNP) rs number, e.g., "rs1800693". The dbSNP is a free public archive for genetic variation within and across different species developed and hosted by the National Center for Biotechnology Information (NCBI) in collaboration with the National Human Genome Research Institute (NHGRI).

A polymorphic site, such as a SNP, is usually preceded by and followed by conserved sequences in the genome of the population of interest and thus the location of a polymorphic site can often be made in reference to a consensus nucleic acid sequence (e.g., of thirty to sixty nucleotides) that bracket the polymorphic site, which in the case of a SNP is commonly referred to as the "SNP context sequence". Context sequences for the SNPs disclosed herein may be found in the NCBI SNP database available at: www.ncbi.nlm.nih.gov/snp. Alternatively, the location of the polymorphic site may be identified by its location in a reference sequence (e.g., GeneBank deposit) relative to the start of the gene, mRNA transcript, BAC clone or even relative to the initiation codon (ATG) for protein translation. The skilled artisan understands that the location of a particular polymorphic site may not occur at precisely the same position in a reference or context sequence in each individual in a population of interest due to the presence of one or more insertions or deletions in that individual's genome as compared to the consensus or reference sequence. It is routine for the skilled artisan to design robust, specific and accurate assays for detecting the alternative alleles at a polymorphic site in any given individual, when the skilled artisan is provided with the identity of the alternative alleles at the polymorphic site to be detected and one or both of a reference sequence or context sequence in which the polymorphic site occurs. Thus, the skilled artisan will understand that specifying the location of any polymorphic site described herein by reference to a particular position in a reference or context sequence (or with respect to an initiation codon in such a sequence) is merely for convenience and that any specifically enumerated nucleotide position literally includes whatever nucleotide position the same polymorphic site is actually located at in the same locus in any individual being tested for the genetic marker of the invention using any of the genotyping methods described herein or other genotyping methods known in the art.

In addition to SNPs, genetic polymorphisms include translocations, insertions, substitutions, deletions, etc., that occur in gene enhancers, exons, introns, promoters, 5' UTR, 3'UTR, etc.

As used herein "rs1800693" refers to a T/C SNP within the sixth intron of the human tumor necrosis factor receptor superfamily, member 1A (TNFRSF1A) gene (GenBank Accession No. NM_001065.3) that is also known as tumor necrosis factor receptor 1 (TNFR1). The TNFRSF1A protein is one of the major receptors for TNFα, and is involved in the NF-kappaB pathway, mediates apoptosis, and regulates inflammation. The rs1800693 polymorphic site is located at Chromosome 12:6330843. The phrase "rs1800693 response allele" as used herein refers to the "C" allele (G allele, in the case of the noncoding strand) or the "T" allele (A allele, in the case of the noncoding strand) at the rs1800693 polymorphic site. In some embodiments of the disclosed methods, uses, and kits, the patient has at least one rs1800693 response allele.

The aforementioned response alleles are useful for the prediction of a DED patient's response to TNFα antagonism. In some embodiments, a DED patient having the CC, CT, or TT genotype is considered likely to respond to treatment with a TNFα antagonist, e.g., a TNFα antibody, such as LME636.

As recognized by the skilled artisan, nucleic acid samples containing a particular SNP may be complementary double stranded molecules and thus reference to a particular site on the sense strand refers as well to the corresponding site on the complementary antisense strand. Similarly, reference to a particular genotype obtained for a SNP on both copies of one strand of a chromosome is equivalent to the complementary genotype obtained for the same SNP on both copies of the other strand. Thus, for example, a T/C genotype for the rs1800693 polymorphic site on the coding strand is equivalent to an A/G genotype for that polymorphic site on the noncoding strand.

As used herein, "genomic sequence" refers to a DNA sequence present in a genome, and includes a region within an allele, an allele itself, or a larger DNA sequence of a chromosome containing an allele of interest.

Products of the DED response markers include nucleic acid products and polypeptide products. "Polypeptide product" refers to a polypeptide encoded by a DED response marker and fragments thereof. "Nucleic acid product" refers to any DNA (e.g., genomic, cDNA, etc.) or RNA (e.g., pre-mRNA, mRNA, miRNA, etc.) products of a DED response markers and fragments thereof.

An "equivalent genetic marker" refers to a genetic marker that is correlated to an allele of interest, e.g., it displays linkage disequilibrium (LD) or is in genetic linkage with the allele of interest. Equivalent genetic markers may be used to determine if a patient has a DED response marker, rather than directly interrogating a biological sample from the patient for the allele per se. Various programs exist to help determine LD for particular SNPs, e.g, HaploBlock (available at bioinfo.cs.technion.ac.il/haploblock/), HapMap, WGA Viewer.

The term "probe" refers to any composition of matter that is useful for specifically detecting another substance, e.g., a substance related to a DED response marker. A probe can be an oligonucleotide (including a conjugated oligonucleotide) that specifically hybridizes to a genomic sequence of a DED response marker, or a nucleic acid product of a DED response marker. A conjugated oligonucleotide refers to an oligonucleotide covalently bound to chromophore or molecules containing a ligand (e.g., an antigen), which is highly specific to a receptor molecule (e.g., an antibody specific to the antigen). The probe can also be a PCR primer, e.g., together with another primer, for amplifying a particular region within a DED response marker. Further, the probe can be an antibody that specifically binds to polypeptide products of these alleles. Further, the probe can be any composition of matter capable of detecting (e.g., binding or hybridizing) an equivalent genetic marker of a DED response marker. In preferred embodiments, the probe specifically hybridizes to a nucleic acid sequence (preferably genomic DNA) or specifically binds to a polypeptide sequence of an allele of interest.

The phrase "specifically hybridizes" is used to refer to hybrization under stringent hybridization conditions. Stringent conditions are known to those skilled in the art and can be found in Current Protocols in Molecular Biology, John Wiley & Sons, N.Y. (1989), 6.3.1-6.3.6. Aqueous and non-aqueous methods are described in that reference and either can be used. One example of stringent hybridization conditions is hybridization in 6× sodium chloride/sodium citrate (SSC) at about 45° C., followed by at least one wash in 0.2×SSC, 0.1% SDS at 50° C. A second example of stringent hybridization conditions is hybridization in 6×SSC at about 45° C., followed by at least one wash in 0.2×SSC, 0.1% SDS at 55° C. Another example of stringent hybridization conditions is hybridization in 6×SSC at about 45° C., followed by at least one wash in 0.2×SSC, 0.1% SDS at 60° C. A further example of stringent hybridization conditions is hybridization in 6×SSC at about 45° C., followed by at least one wash in 0.2×SSC, 0.1% SDS at 65° C. High stringent conditions include hybridization in 0.5 M sodium phosphate, 7% SDS at 65° C., followed by at least one wash at 0.2×SSC, 1% SDS at 65° C.

The phrase "a region of a nucleic acid" is used to indicate a smaller sequence within a larger sequence of nucleic acids. For example, a gene is a region of a chromosome, an exon is a region of a gene, etc.

The term "specifically binds" in the context of polypeptides is used to mean that a probe binds a given polypeptide target (e.g., a polypeptide product a DED response marker) rather than randomly binding undesireable polypeptides. However, "specifically binds" does not exclude some cross reactivity with undesireable polypeptides, as long as that cross reactivity does not interfere with the capability of the probe to provide a useful measure of the presence of the given polypeptide target.

The term "capable" is used to mean that ability to achieve a given result, e.g., a probe that is capable of detecting the presence of a particular substance means that the probe may be used to detect the particular substance.

An "oliogonucelotide" refers to a short sequence of nucleotides, e.g., 2-100 bases.

The term "biological sample" as used herein refers to a sample from a patient, which may be used for the purpose of identification, diagnosis, prediction, or monitoring. Preferred samples include synovial fluid, blood, blood-derived product (such as buffy coat, serum, and plasma), lymph, urine, tear, saliva, hair bulb cells, cerebrospinal fluid, buccal swabs, feces, synovial fluid, synovial cells, sputum, or tissue samples (e.g., cartilage samples). In addition, one of skill in the art would realize that some samples would be more readily analyzed following a fractionation or purification procedure, for example, isolation of DNA from whole blood.

TNFα Antagonists

The various disclosed pharmaceutical compositions, regimens, processes, uses, methods and kits utilize an TNFα antagonist, e.g., TNFα binding molecule (e.g., TNFα antibody or antigen-binding portion thereof, e.g., LME636) or TNFα receptor binding molecule (e.g., TNFα receptor antibody or antigen-binding portion thereof).

In one embodiment, the TNFα antagonist, e.g., TNFα binding molecule (e.g., TNFα antibody or antigen-binding portion thereof, e.g., LME636) comprises at least one heavy chain variable domain ($V_H$) comprising hypervariable regions CDRH1, CDRH2 and CDRH3, said CDRH1 having the amino acid sequence SEQ ID NO:1, said CDRH2 having the amino acid sequence SEQ ID NO:2, and said CDRH3 having the amino acid sequence SEQ ID NO:3. In one embodiment, the TNFα antagonist, e.g., TNFα binding molecule (e.g., TNFα antibody or antigen-binding portion thereof, e.g., LME636) comprises at least one light chain variable domain ($V_L$) comprising hypervariable regions CDRL1, CDRL2 and CDRL3, said CDRL1 having the amino acid sequence SEQ ID NO:4, said CDRL2 having the amino acid sequence SEQ ID NO:5 and said CDRL3 having the amino acid sequence SEQ ID NO:6.

In one embodiment, the TNFα antagonist, e.g., TNFα binding molecule (e.g., TNFα antibody or antigen-binding portion thereof, e.g., LME636) comprises a $V_H$ domain and a $V_L$ domain, wherein: a) the $V_H$ domain comprises (e.g., in sequence): i) hypervariable regions CDRH1, CDRH2 and CDRH3, said CDRH1 having the amino acid sequence SEQ ID NO:1, said CDRH2 having the amino acid sequence SEQ ID NO:2, and said CDRH3 having the amino acid sequence SEQ ID NO:3; and b) the V$_L$ domain comprises (e.g., in sequence) hypervariable regions CDRL1, CDRL2 and CDRL3, said CDRL1 having the amino acid sequence SEQ ID NO:4, said CDRL2 having the amino acid sequence SEQ ID NO:5, and said CDRL3 having the amino acid sequence SEQ ID NO:6.

In one embodiment, the TNFα antagonist, e.g., TNFα binding molecule (e.g., TNFα antibody or antigen-binding portion thereof, e.g., LME636) comprises: a) a heavy chain variable domain (V$_H$) comprising the amino acid sequence set forth as SEQ ID NO:8; b) a light chain variable domain (V$_L$) comprising the amino acid sequence set forth as SEQ ID NO:10; c) a V$_H$ domain comprising the amino acid sequence set forth as SEQ ID NO:8 and a V$_L$ domain comprising the amino acid sequence set forth as SEQ ID NO:10; d) a V$_H$ domain comprising the hypervariable regions set forth as SEQ ID NO:1, SEQ ID NO:2, and SEQ ID NO:3; e) a V$_L$ domain comprising the hypervariable regions set forth as SEQ ID NO:4, SEQ ID NO: 5 and SEQ ID NO:6; or f) a V$_H$ domain comprising the hypervariable regions set forth as SEQ ID NO:1, SEQ ID NO:2, and SEQ ID NO:3 and a V$_L$ domain comprising the hypervariable regions set forth as SEQ ID NO:4, SEQ ID NO:5 and SEQ ID NO:6.

For ease of reference the amino acid sequences of the hypervariable regions of the LME636 scFv antibody is provided in Table 2, below.

TABLE 2

| Light-Chain | |
| --- | --- |
| CDRL1 | QSSQSVYGNIWMA (SEQ ID NO: 4) |
| CDRL2 | QASKLAS (SEQ ID NO: 5) |
| CDRL3 | QGNFNTGDRYA (SEQ ID NO: 6) |
| Variable Light Chain | EIVMTQSPSTLSASVGDRVIITCQSSQSVYGNIWMAWYQ KQPGRAPKLLIYQASKLASGVPSRFSGSGSGAEFTLTIS SLQPDDFATYYCQGNFNTGDRYAFGQGTKLTVLG (SEQ ID NO: 7) |

| Heavy-Chain | |
| --- | --- |
| CDRH1 | GFTISRSYWIC (SEQ ID NO: 1) |
| CDRH2 | CIYGDNDITPLYANWAKG (SEQ ID NO: 2) |
| CDRH3 | LGYADYAYDL (SEQ ID NO: 3) |
| Variable Heavy Chain | EVQLVESGGGSVQPGGSLRLSCTASGFTISRSYWICWVR QAPGKGLEWVGCIYGDNDITPLYANWAKGRFTISRDTSK NTVYLQMNSLRAEDTATYYCARLGYADYAYDLWGQGTTV TVSS (SEQ ID NO: 8) |

In some embodiments, the TNFα antagonist, e.g., TNFα binding molecule (e.g., TNFα antibody or antigen-binding portion thereof, e.g., LME636) comprises the light chain of SEQ ID NO: 7. In other embodiments, the TNFα antagonist comprises the heavy chain of SEQ ID NO: 8. In other embodiments, the TNFα 7 antagonist comprises the light chain of SEQ ID NO: 7 and the heavy chain of SEQ ID NO: 8. In some embodiments, the TNFα antagonist comprises the three CDRs of SEQ ID NO: 7. In other embodiments, the TNFα antagonist comprises the three CDRs of SEQ ID NO: 8. In other embodiments, the TNFα antagonist comprises the three CDRs of SEQ ID NO: 7 and the three CDRs of SEQ ID NO: 8. CDRs of SEQ ID NO: 7 and SEQ ID NO: 8, are shown in Table 2. In other embodiments, the TNFα antagonist comprises the sequence of SEQ ID NO: 9:

```
                                      (SEQ ID NO: 9)
EIVMTQSPSTLSASVGDRVIITCQSSQSVYGNIWMAWYQQKPGRAPKLLI

YQASKLASGVPSRFSGSGSGAEFTLTISSLQPDDFATYYCQGNFNTGDRY

AFGQGTKLTVLGGGGGSGGGGSGGGGSGGGGSEVQLVESGGGSVQPGGSL

RLSCTASGFTISRSYWICWVRQAPGKGLEWVGCIYGDNDITPLYANWAKG

RFTISRDTSKNTVYLQMNSLRAEDTATYYCARLGYADYAYDLWGQGTTVT

VSS.
```

Hypervariable regions may be associated with any kind of framework regions, though preferably are of human origin. Suitable framework regions are described in Kabat E. A. et al, ibid. The preferred heavy chain framework is the heavy chain framework of the LME636 antibody as shown in SEQ ID NO: 0.10:

```
                                     (SEQ ID NO: 10)
EVQLVESGGGLVQPGGSLRLSCTAS(X)$_{n=3-50}$WVRQAPGKGLEWVG(X)

$_{n=3-50}$RFTISRDTSKNTVYLQMNSLRAEDTAVYYCAR(X)$_{n=3-50}$WGQGTLVTVSS.
```

The preferred light chain framework is the light chain framework of the LME636 antibody as shown in SEQ ID NO: 0.11:

```
                                     (SEQ ID NO: 11)
EIVMTQSPSTLSASVGDRVIITC(X)$_{n=3-50}$WYQQKPGKAPKLLIY(X)$_{n=3-50}$

GVPSRFSGSGSGTEFTLTISSLQPDDFATYYC(X)$_{n=3-50}$FGQGTKLTVLG.
```

As used in the sequences of SEQ ID NO: 10 and SEQ ID NO: 11, (X)$_{n=3-50}$ represents a CDR.

In one embodiment, the TNFα antagonist, e.g., TNFα binding molecule (e.g., TNFα antibody or antigen-binding portion thereof, e.g., LME636) is selected from a single chain binding molecule which comprises an antigen binding site comprising: a) a first domain comprising in sequence the hypervariable regions CDRH1, CDRH2 and CDRH3, said CDRH1 having the amino acid sequence SEQ ID NO:1, said CDRH2 having the amino acid sequence SEQ ID NO:2, and said CDRH3 having the amino acid sequence SEQ ID NO:3; and b) a second domain comprising the hypervariable regions CDRL1, CDRL2 and CDRL3, said CDRL1 having the amino acid sequence SEQ ID NO:4, said CDRL2 having the amino acid sequence SEQ ID NO:5, and said CDRL3 having the amino acid sequence SEQ ID NO:6; and c) a peptide linker which is bound either to the N-terminal extremity of the first domain and to the C-terminal extremity of the second domain or to the C-terminal extremity of the first domain and to the N-terminal extremity of the second domain.

Alternatively, a TNFα antagonist, e.g., TNFα binding molecule (e.g., TNFα antibody or antigen-binding portion thereof) for use in the disclosed methods may comprise a derivative of the TNFα binding molecules set forth herein by sequence (e.g., a pegylated version of LME636). Alternatively, the V$_H$ or V$_L$ domain of a TNFα antagonist, e.g., TNFα binding molecule (e.g., TNFα antibody or antigen-binding portion thereof) for use in the disclosed methods may have V$_H$ or V$_L$ domains that are substantially identical to the V$_H$ or V$_L$ domains set forth herein (e.g., those set forth in SEQ ID NO:8 and 7). An anti-TNFα antibody disclosed herein may comprise a heavy chain that is substantially identical to that set forth as SEQ ID NO: 8 and/or a light chain that is substantially identical to that set forth as SEQ ID NO: 7. An anti-TNFα antibody disclosed herein may comprise a heavy chain that comprises SEQ ID NO: 8 and a light chain that comprises SEQ ID NO: 7. An anti-TNFα antibody disclosed herein may comprise: a) one heavy chain which comprises a variable domain having an amino acid sequence substantially identical to that shown in SEQ ID NO: 8 and the constant part of a human heavy chain; and b) one light chain which comprises a variable domain having an amino acid sequence substantially identical to that shown in SEQ ID NO: 7 and the constant part of a human light chain. Alternatively, a TNFα antagonist, e.g., TNFα binding molecule (e.g., TNFα antibody or antigen-binding portion thereof) for use in the disclosed methods may be an amino acid sequence variant of the reference TNFα binding molecules set forth herein. In all such cases of derivative and variants, the TNFα antagonist is capable of inhibiting the activity of about 1 nM (=30 ng/ml) human TNFα at a concentration of about 50 nM or less, about 20 nM or less, about 10 nM or less, about 5 nM or less, or more preferably of about 3 nM or less of said molecule by 50%, said inhibitory activity being measured, for example, by assaying for neutralization of TNFα cytotoxicity of L929 cells as described in Chiu et al., 2011, PLoS ONE, Vol 6, issue 1, e16373.

The disclosure also includes TNFα antagonists, e.g., TNFα binding molecules (e.g., TNFα antibody or antigen-binding portion thereof, e.g., LME636) in which one or more of the amino acid residues of CDRH1, CDRH2, CDRH3, CDRL1, CDRL2, CDRL3, or the frameworks, typically only a few (e.g., 1-4), are changed; for instance by mutation, e.g., site directed mutagenesis of the corresponding DNA sequences. The disclosure includes the DNA sequences coding for such changed TNFα antagonists.

The disclosure also includes TNFα antagonists, e.g., TNFα binding molecules (e.g., TNFα antibody or antigen-binding portion thereof, e.g., LME636) that have binding specificity for human TNFα, in particular TNFα antibodies capable of inhibiting the binding of TNFα to its receptor and TNFα antibodies capable of inhibiting the activity of 1 nM (=30 ng/ml) human TNFα at a concentration of about 50 nM or less, about 20 nM or less, about 10 nM or less, about 5 nM or less, or more preferably of about 3 nM or less of said molecule by 50% (said inhibitory activity being measured by assaying for neutralization of TNFα cytotoxicity of L929 cells).

In a preferred embodiment, the anti-TNFα antibodies for use in the disclosed methods, uses, kits, etc. is LME636, which comprises the sequence of SEQ ID NO: 9. LME636 is a humanized monoclonal scFv antibody fragment consisting of 254 amino acids (molecular mass: 26.7 kDa) that inhibits human TNFα, and is recombinantly produced in *E. coli* by standard expression technology. The molecule was genetically engineered by grafting the complementarity determining regions (CDRs) and specific framework residues from light and heavy chain variable region sequences of a monoclonal rabbit anti-human TNFα antibody to human light and heavy chain variable region frameworks, covalently linked by a flexible amino acid sequence consisting of glycine and serine.

In one embodiment, a methionine derived from the start codon in an expression vector is present in the final protein in cases where it has not been cleaved posttranslationally. In that case, LME636 has the sequence of SEQ ID NO: 12:

(SEQ ID NO: 12)
MEIVMTQSPSTLSASVGDRVIITCQSSQSVYGNIWMAWYQQKPGRAPKLL

IYQASKLASGVPSRFSGSGSGAEFTLTISSLQPDDFATYYCQGNFNTGDR

YAFGQGTKLTVLGGGGSGGGGSGGGGSGGGGSEVQLVESGGGSVQPGGS

LRLSCTASGFTISRSYWICWVRQAPGKGLEWVGCIYGDNDITPLYANWAK

GRFTISRDTSKNTVYLQMNSLRAEDTATYYCARLGYADYAYDLWGQGTTV

TVSS.

Other preferred TNFα antibodies for use in the disclosed methods, kits and uses are those set forth in WO 2009/155723 and WO 2012/051734.

Techniques for Assaying, Diagnostic Methods and Methods of Producing a Transmittable Form of Information The disclosed methods are useful for the treatment or amelioration of DED, as well as predicting the likelihood of a DED patient's response to treatment with a TNFα antagonist, e.g., LME636. These methods employ, inter alia, determining whether a patient has a DED response marker in a sample from the patient.

A biological sample from the patient may be assayed for the presence of a DED response marker by any applicable conventional means, which will be selected depending on whether the particular marker falls within an exon, an intron, a non-coding portion of mRNA or a non-conding genomic sequence.

Numerous biological samples may be used to identify the presence of alleles or proteins, the level of expression of genes or proteins, and the activity of a protein, e.g., blood, synovial fluid, buffy coat, serum, plasma, lymph, feces, urine, tear, saliva, cerebrospinal fluid, buccal swabs, sputum, or tissue. Various sources within a biological sample may be used in the disclosed methods, e.g., one may assay genomic DNA obtained from a biological sample to detect a DED response marker, or one may assay products of a DED response marker, e.g., nucleic acid products (e.g., DNA, pre-mRNA, mRNA, micro RNAs, etc.) and polypeptide products (e.g., expressed proteins) obtained from a biological sample.

We have determined that the various SNP alleles of Table 1 are useful for predicting certain patient's response to treatment by TNFα antagonism (e.g., using LME636). In preferred embodiments, a genomic sequence of a DED response marker is analyzed to determine whether a subject has a DED response marker.

As described in the Examples, our most recent findings lead to the conclusion that the presence of a genotype associated with the SNP rs1800693 may be useful to predict improved response to TNFα antagonism (e.g., LME636) for DED. The presence of a DED response marker may be detected by a variety of genotyping techniques. Typically, such genotyping techniques employ one or more oligonucleotides that are complementary to a region containing, or adjacent to, the polymorphic site (e.g., SNP) of interest. The sequence of an oligonucleotide used for genotyping a particular polymorphic site of interest is typically designed based on a context sequence or a reference sequence.

Numerous methods and devices are available to identify the presence of a DED response marker. DNA (genomic and cDNA) for SNP detection can be prepared from a biological sample by methods well known in the art, e.g., phenol/chloroform extraction, PUREGENE DNA® purification system from GentAS Systems (Qiagen, CA). Detection of a DNA sequence may include examining the nucleotide(s)

located at either the sense or the anti-sense strand within that region. The presence of polymorphisms in a patient may be detected from DNA (genomic or cDNA) obtained from PCR using sequence-specific probes, e.g., hydrolysis probes from Taqman, Beacons, Scorpions; or hybridization probes that detect the marker or polymorphism. For the detection of the polymorphism, sequence specific probes may be designed such that they specifically hybridize to the genomic DNA for the alleles of interest or, in some cases, an RNA of interest. Primers and probes for polymorphic sites (e.g., SNP) may be designed based on context sequences found in the NCBI SNP database available at: www.ncbi.nlm.nih.gov/snp. These probes may be labeled for direct detection or contacted by a second, detectable molecule that specifically binds to the probe. The PCR products also can be detected by DNA-binding agents. Said PCR products can then be subsequently sequenced by any DNA sequencing method available in the art. Alternatively the presence of allele can be detected by sequencing using any sequencing methods such as, but not limited to, Sanger-based sequencing, pyrosequencing or next generation sequencing (Shendure J. and Ji, H., Nature Biotechnology (1998), Vol. 26, Nr 10, pages 1135-1145). Optimised allelic discrimination assays for SNPs may be purchased from Applied Biosystems (Foster City, Calif., USA).

Various techniques can be applied to interrogate a particular polymorphism (e.g., SNP), including, e.g., hybridization-based methods, such as dynamic allele-specific hybridization (DASH) genotyping, polymorphic site (e.g., SNP) detection through molecular beacons (Abravaya K., et al. (2003) Clin Chem Lab Med. 41:468-474), Luminex xMAP Technology®, Illumina Golden Gate® technology and commercially available high-density oligonucleotide SNP arrays (e.g., the Affymetrix Human SNP 5.0 GeneChip® performs a genome-wide assay that can genotype over 500,000 human SNPs), BeadChip® kits from Illumina, e.g, Human660W-Quad and Human 1.2M-Duo); enzyme-based methods, such as restriction fragment length polymorphism (RFLP), PCR-based methods (e.g., Tetra-primer ARMS-PCR), Invader assays (Olivier M. (2005) Mutat Res. 573(1-2):103-10), various primer extension assays (incorporated into detection formats, e.g., MALDI-TOF Mass spectrometry, electrophoresis, blotting, and ELISA-like methods), TaqMan® assays, and oligonucleotide ligase assays; and other post-amplification methods, e.g., analysis of single strand conformation polymorphism (Costabile et al. (2006) Hum. Mutat. 27(12):1163-73), temperature gradient gel electrophoresis (TGGE), denaturing high performance liquid chromatography, high-resolution melting analysis, DNA mismatch-binding protein assays (e.g., MutS protein from *Thermus aquaticus* binds different single nucleotide mismatches with different affinities and can be used in capillary electrophoresis to differentiate all six sets of mismatches), SNPLex® (proprietary SNP detecting system available from Applied Biosystems), capillary electrophoresis, mass spectrometry, and various sequencing methods, e.g., pyrosequencing and next generation sequencing, etc. Commercial kits for SNP genotyping include, e.g., Fluidigm Dynamic Array® IFCs (Fluidigm), TaqMan® SNP Genotyping Assay (Applied Biosystems), MassARRAY® iPLEX Gold (Sequenom), Type-it Fast® SNP Probe PCR Kit (Quiagen), etc.

In some embodiments, the presence of a polymorphic site (e.g., SNP) in a patient is detected using a hybridization assay. In a hybridization assay, the presence of the genetic marker is determined based on the ability of the nucleic acid from the sample to hybridize to a complementary nucleic acid molecule, e.g., an oligonucleotide probe. A variety of hybridization assays are available. In some, hybridization of a probe to the sequence of interest is detected directly by visualizing a bound probe, e.g., a Northern or Southern assay. In these assays, DNA (Southern) or RNA (Northern) is isolated. The DNA or RNA is then cleaved with a series of restriction enzymes that cleave infrequently in the genome and not near any of the markers being assayed. The DNA or RNA is then separated, e.g., on an agarose gel, and transferred to a membrane. A labeled probe or probes, e.g., by incorporating a radionucleotide or binding agent (e.g., SYBR® Green), is allowed to contact the membrane under low-, medium- or high-stringency conditions. Unbound probe is removed and the presence of binding is detected by visualizing the labeled probe. In some embodiments, arrays, e.g., the MassARRAY® system (Sequenom, San Diego, Calif., USA) may be used to genotype a subject.

Traditional genotyping methods may also be modified for use in genotyping. Such traditional methods include, e.g., DNA amplification techniques such as PCR and variants thereof, direct sequencing, SSO hybridization coupled with the Luminex xMAP® technology, SSP typing, and SBT.

Sequence-Specific Oligonucleotide (SSO) typing uses PCR target amplification, hybridization of PCR products to a panel of immobilized sequence-specific oligonucleotides on the beads, detection of probe-bound amplified product by color formation followed by data analysis. Those skilled in the art would understand that the described Sequence-Specific Oligonucleotide (SSO) hybridization may be performed using various commercially available kits, such as those provided by One Lambda, Inc. (Canoga Park, Calif.) or Lifecodes HLA Typing Kits (Tepnel Life Sciences Corp.) coupled with Luminex® technology (Luminex, Corporation, TX). LABType® SSO is a reverse SSO (rSSO) DNA typing solution that uses sequence—specific oligonucleotide (SSO) probes and color-coded microspheres to identify HLA alleles. The target DNA is amplified by polymerase chain reactions (PCR) and then hybridized with the bead probe array. The assay takes place in a single well of a 96-well PCR plate; thus, 96 samples can be processed at one time.

Sequence Specific Primers (SSP) typing is a PCR based technique which uses sequence specific primers for DNA based typing. The SSP method is based on the principle that only primers with completely matched sequences to the target sequences result in amplified products under controlled PCR conditions. Allele sequence-specific primer pairs are designed to selectively amplify target sequences which are specific to a single allele or group of alleles. PCR products can be visualized on agarose gel. Control primer pairs that matches non-allelic sequences present in all samples act as an internal PCR control to verify the efficiency of the PCR amplification. Those skilled in the art would understand that low, medium and high resolution genotyping with the described sequence-specific primer typing may be performed using various commercially available kits, such as the Olerup SSP™ kits (Olerup, Pa.) or (Invitrogen) or Allset and ™Gold DQA1 Low resolution SSP (Invitrogen).

Sequence Based Typing (SBT) is based on PCR target amplification, followed by sequencing of the PCR products and data analysis.

In some cases, RNA, e.g., mature mRNA, pre-mRNA, can also be used to determine the presence of particular polymorphisms (see Table 1). Analysis of the sequence of mRNA transcribed from a given gene can be performed using any known method in the art including, but not limited, to Northern blot analysis, nuclease protection assays (NPA), in situ hybridization, reverse transcription-polymerase chain reaction (RT-PCR), RT-PCR ELISA, TaqMan-based quantitative RT-PCR (probe-based quantitative RT-PCR) and SYBR green-based quantitative RT-PCR. In one example, detection of mRNA levels involves contacting the isolated mRNA with an oligonucleotide that can hybridize to mRNA encoded by a DED response marker. The nucleic acid probe can typically be, for example, a full-length cDNA, or a portion thereof, such as an oligonucleotide of at least 7, 15, 30, 50, or 100 nucleotides in length and sufficient to specifically hybridize under stringent conditions to the mRNA. Hybridization of an mRNA with the probe indicates that the marker in question is being expressed. In one format, the RNA is immobilized on a solid surface and contacted with a probe, for example by running the isolated RNA on an agarose gel and transferring the mRNA from the gel to a membrane, such as nitrocellulose. Amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers. PCR products can be detected by any suitable method including, but not limited to, gel electrophoresis and staining with a DNA-specific stain or hybridization to a labeled probe.

In some cases, the presence of a polymorphism in a patient can be determined by analyzing polypeptide products of the DED response markers (see Table 1). Detection of polypeptide products can be performed using any known method in the art including, but not limited to, immunocytochemical staining, ELISA, flow cytometry, Western blot, spectrophotometry, HPLC, and mass spectrometry.

One method for detecting polypeptide products in a sample is by means of a probe that is a binding protein capable of interacting specifically with a marker protein (e.g., an antibody). Preferably, labeled antibodies, binding portions thereof, or other binding partners can be used. The antibodies can be monoclonal or polyclonal in origin, or may be biosynthetically produced. The binding partners may also be naturally occurring molecules or synthetically produced. The amount of complexed proteins is determined using standard protein detection methodologies described in the art. A detailed review of immunological assay design, theory and protocols can be found in numerous texts in the art, including Practical Immunology, Butt, W. R., ed., Marcel Dekker, New York, 1984. A variety of assays are available for detecting proteins with labeled antibodies. Direct labels include fluorescent or luminescent tags, metals, dyes, radionuclides, and the like, attached to the antibody. Indirect labels include various enzymes well known in the art, such as alkaline phosphatase, hydrogen peroxidase and the like. In a one-step assay, polypeptide products, if present, are immobilized and incubated with a labeled antibody. The labeled antibody binds to the immobilized target molecule. After washing to remove unbound molecules, the sample is assayed for the label.

The use of immobilized antibodies specific for the proteins or polypeptides is also contemplated by the present disclosure. The antibodies can be immobilized onto a variety of solid supports, such as magnetic or chromatographic matrix particles, the surface of an assay place (such as microtiter wells), pieces of a solid substrate material (such as plastic, nylon, paper), and the like. An assay strip can be prepared by coating the antibody or a plurality of antibodies in an array on solid support. This strip can then be dipped into the test sample and then processed quickly through washes and detection steps to generate a measurable signal, such as a colored spot.

In a two-step assay, immobilized polypeptide products of a DED response marker may be incubated with an unlabeled antibody. The unlabeled antibody complex, if present, is then bound to a second, labeled antibody that is specific for the unlabeled antibody. The sample is washed and assayed for the presence of the label. The choice of marker used to label the antibodies will vary depending upon the application. However, the choice of the marker is readily determinable to one skilled in the art. The antibodies may be labeled with a radioactive atom, an enzyme, a chromophoric or fluorescent moiety, or a colorimetric tag. The choice of tagging label also will depend on the detection limitations desired. Enzyme assays (ELISAs) typically allow detection of a colored product formed by interaction of the enzyme-tagged complex with an enzyme substrate. Some examples of radioactive atoms include $^{32}P$, $^{125}I$, $^{3}H$, and $^{14}P$. Some examples of enzymes include horseradish peroxidase, alkaline phosphatase, beta-galactosidase, and glucose-6-phosphate dehydrogenase. Some examples of chromophoric moieties include fluorescein and rhodamine. The antibodies may be conjugated to these labels by methods known in the art. For example, enzymes and chromophoric molecules may be conjugated to the antibodies by means of coupling agents, such as dialdehydes, carbodiimides, dimaleimides, and the like. Alternatively, conjugation may occur through a ligand-receptor pair. Some suitable ligand-receptor pairs include, for example, biotin-avidin or -streptavidin, and antibody-antigen.

In one aspect, the present disclosure contemplates the use of a sandwich technique for detecting polypeptide products in biological samples. The technique requires two antibodies capable of binding the protein of interest: e.g., one immobilized onto a solid support and one free in solution, but labeled with some easily detectable chemical compound. Examples of chemical labels that may be used for the second antibody include but are not limited to radioisotopes, fluorescent compounds, and enzymes or other molecules which generate colored or electrochemically active products when exposed to a reactant or enzyme substrate. When samples containing polypeptide products are placed in this system, the polypeptide products binds to both the immobilized antibody and the labeled antibody. The result is a "sandwich" immune complex on the support's surface. The complexed protein is detected by washing away nonbound sample components and excess labeled antibody, and measuring the amount of labeled antibody complexed to protein on the support's surface. The sandwich immunoassay is highly specific and very sensitive, provided that labels with good limits of detection are used.

Preferably, the presence of polypeptide products in a sample is detected by radioimmunoassays or enzyme-linked immunoassays, competitive binding enzyme-linked immunoassays, dot blot, Western blot, chromatography, preferably high performance liquid chromatography (HPLC), or other assays known in the art. Specific immunological binding of the antibody to the protein or polypeptide can be detected directly or indirectly.

Dot blotting is routinely practiced by the skilled artisan to detect a desired protein using an antibody as a probe (Promega Protocols and Applications Guide, Second Edition, 1991, Page 263, Promega Corporation). Samples are applied to a membrane using a dot blot apparatus. A labeled probe is incubated with the membrane, and the presence of the protein is detected.

Western blot analysis is well known to the skilled artisan (Sambrook et al., Molecular Cloning, A Laboratory Manual, 1989, Vol. 3, Chapter 18, Cold Spring Harbor Laboratory). In Western blot, the sample is separated by SDS-PAGE. The gel is transferred to a membrane. The membrane is incubated with labeled antibody for detection of the desired protein.

The assays described above involve steps such as but not limited to, immunoblotting, immunodiffusion, immunoelectrophoresis, or immunoprecipitation. In some embodiments, an automatic analyzer is used to determine the presence of a DED response marker.

Disclosed herein are methods of predicting the likelihood that a patient having DED will respond to treatment with a TNFα antagonist, comprising detecting the presence or absence of a DED response marker in a biological sample from the patient, wherein: a) the presence of the DED response marker is indicative of an increased likelihood that the patient will respond to treatment with the TNFα antagonist; and b) the absence of the DED response marker is indicative of a decreased likelihood that the patient will respond to treatment with the TNFα antagonist.

In some embodiments, the method further comprises the step of obtaining the biological sample from the patient, wherein the step of obtaining is performed prior to the step of assaying.

In some embodiments, the DED response marker is detected by assaying the biological sample for a nucleic acid product of the DED response marker, a polypeptide product of the DED response marker, or an equivalent genetic marker of the DED response marker. In some embodiments, the DED response marker is detected by assaying the biological sample for a genomic sequence of the DED response marker. In some embodiments, the biological sample is selected from the group consisting of synovial fluid, blood, serum, feces, plasma, urine, tear, saliva, cerebrospinal fluid, a leukocyte sample and a tissue sample.

In some embodiments, the presence of the DED response marker is detected by a technique selected from the group consisting of Northern blot analysis, polymerase chain reaction (PCR), reverse transcription-polymerase chain reaction (RT-PCR), TaqMan-based assays, direct sequencing, dynamic allele-specific hybridization, high-density oligonucleotide SNP arrays, restriction fragment length polymorphism (RFLP) assays, primer extension assays, oligonucleotide ligase assays, analysis of single strand conformation polymorphism, temperature gradient gel electrophoresis (TGGE), denaturing high performance liquid chromatography, high-resolution melting analysis, DNA mismatch-binding protein assays, SNPLex®, capillary electrophoresis, Southern Blot, immunoassays, immunohistochemistry, ELISA, flow cytometry, Western blot, HPLC, and mass spectrometry.

In some embodiments of the disclosed methods and uses, the TNFα antagonist is an TNFα binding molecule or an TNFα receptor binding molecule. In some embodiments, the TNFα binding molecule or an TNFα receptor binding molecule is an TNFα binding molecule. In some embodiments, the TNFα binding molecule is a TNFα antibody or antigen-binding portion thereof.

In some embodiments of the disclosed methods and uses, the TNFα antibody is a recombinant humanized antibody. In some embodiments of the disclosed methods and uses, the recombinant humanized TNFα antibody is LME636.

Methods of Treatment and Uses of TNFα Antagonists

The disclosed methods allow clinicians to provide a personalized therapy for DED patients, i.e., they allow determination of whether to selectively treat the patient with a TNFα antagonist (e.g., LME636) or whether to selectively treat the patient with an over the counter treatment or topical cyclosporine. In this way, a clinician can maximize the benefit and minimize the risk of TNFα antagonism in the entire population of patients afflicted with DED. It will be understood that TNFα antagonists, e.g., TNFα binding molecules (e.g., TNFα antibody or antigen-binding portion thereof, e.g., LME636) or TNFα receptor binding molecules (e.g., TNFα receptor antibody or antigen-binding portion thereof) are useful for the treatment, prevention, or amelioration of DED (e.g., signs and symptoms & structural changes, improving ocular discomfort, etc.) as disclosed herein, particularly in patients that have a DED response marker.

The TNFα antagonists, e.g., TNFα binding molecules (e.g., TNFα antibody or antigen-binding portion thereof, e.g., LME636) or TNFα receptor binding molecules (e.g., TNFα receptor antibody or antigen-binding portion thereof), may be used in vitro, ex vivo, or incorporated into pharmaceutical compositions and administered to individuals (e.g., human patients) in vivo to treat, ameliorate, or prevent DED, e.g., in patients who have a DED response marker. A pharmaceutical composition will be formulated to be compatible with its intended route of administration (e.g., oral compositions generally include an inert diluent or an edible carrier). Other nonlimiting examples of routes of administration include parenteral (e.g., intravenous), intradermal, subcutaneous, oral (e.g., inhalation), transdermal (topical), transmucosal, and rectal administration. The pharmaceutical compositions compatible with each intended route are well known in the art.

The TNFα antagonists, e.g., TNFα binding molecules (e.g., TNFα antibody or antigen-binding portion thereof, e.g., LME636) or TNFα receptor binding molecules (e.g., TNFα receptor antibody or antigen-binding portion thereof), may be used as a pharmaceutical composition when combined with a pharmaceutically acceptable carrier. Such a composition may contain, in addition to a TNFα antagonist, carriers, various diluents, fillers, salts, buffers, stabilizers, solubilizers, and other materials well known in the art. The characteristics of the carrier will depend on the route of administration. The pharmaceutical compositions for use in the disclosed methods may also contain additional therapeutic agents for treatment of the particular targeted disorder. For example, a pharmaceutical composition may also include other anti-inflammatory agents. Such additional factors and/or agents may be included in the pharmaceutical composition to produce a synergistic effect with the TNFα binding molecules, or to minimize side effects caused by the TNFα antagonists, e.g., TNFα binding molecules (e.g., TNFα antibody or antigen-binding portion thereof, e.g., LME636) or TNFα receptor binding molecules (e.g., TNFα receptor antibody or antigen-binding portion thereof).

Pharmaceutical compositions for use in the disclosed methods may be manufactured in conventional manner. In one embodiment, the pharmaceutical composition is provided in lyophilized form. For immediate administration it is dissolved in a suitable aqueous carrier, for example sterile water for injection or sterile buffered physiological saline. If it is considered desirable to make up a solution of larger volume for administration by infusion rather than a bolus injection, may be advantageous to incorporate human serum albumin or the patient's own heparinised blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution. Other formulations comprise liquid or lyophilized formulation.

Antibodies, e.g., antibodies to TNFα, are typically formulated either in aqueous form ready for parenteral administration or as lyophilisates for reconstitution with a suitable diluent prior to administration. In some embodiments of the disclosed methods and uses, the TNFα antagonist, e.g., TNFα antibody, e.g., LME636, is formulated as a lyophilisate. Suitable lyophilisate formulations can be reconstituted in a small liquid volume (e.g., 2 ml or less) to allow subcutaneous administration and can provide solutions with low levels of antibody aggregation.

The appropriate dosage will, of course, vary depending upon, for example, the particular TNFα antagonists, e.g., TNFα binding molecules (e.g., TNFα antibody or antigen-binding portion thereof, e.g., LME636) or TNFα receptor binding molecules (e.g., TNFα receptor antibody or antigen-binding portion thereof) to be employed, the host, the mode of administration and the nature and severity of the condition being treated, and on the nature of prior treatments that the patient has undergone. Ultimately, the attending health care provider will decide the amount of the TNFα antagonist with which to treat each individual patient. In some embodiments, the attending health care provider may administer low doses of the TNFα antagonist and observe the patient's response. In other embodiments, the initial dose(s) of TNFα antagonist administered to a patient are high, and then are titrated downward until signs of relapse occur. Larger doses of the TNFα antagonist may be administered until the optimal therapeutic effect is obtained for the patient, and the dosage is not generally increased further.

In practicing some of the methods of treatment or uses of the present disclosure, a therapeutically effective amount of a TNFα antagonists, e.g., TNFα binding molecules (e.g., TNFα antibody or antigen-binding portion thereof, e.g., LME636) or TNFα receptor binding molecule (e.g., TNFα antibody or antigen-binding portion thereof) is administered to a patient, e.g., a mammal (e.g., a human). While it is understood that the disclosed methods provide for selective treatment of patients (i.e., patients having DED) depending on the presence of a DED response marker, this does not preclude that, if the patient is ultimately treated with a TNFα antagonist, such TNFα antagonist therapy is necessarily a monotherapy. Indeed, if a patient is selected for treatment with a TNFα antagonist, then the TNFα antagonist (e.g., LME636) may be administered in accordance with the method of the disclosure either alone or in combination with other therapeutics for treating DED in patients. When coadministered with one or more additional therapeutics, a TNFα antagonist may be administered either simultaneously with the other therapeutic, or sequentially. If administered sequentially, the attending physician will decide on the appropriate sequence of administering the TNFα antagonist in combination with other therapeutics, as well as the appropriate dosages for co-delivery.

A TNFα antagonist can be conveniently administered parenterally, intravenously, e.g., into the antecubital or other peripheral vein, intramuscularly, or subcutaneously. The duration of intravenous (i.v.) therapy using a pharmaceutical composition of the present disclosure will vary, depending on the severity of the disease being treated and the condition and personal response of each individual patient. Also contemplated is subcutaneous (s.c.) therapy using a pharmaceutical composition of the present disclosure. The health care provider will decide on the appropriate duration of i.v. or s.c. therapy and the timing of administration of the therapy, using the pharmaceutical composition of the present disclosure.

In certain embodiments, a TNFα antagonist, e.g., LME636, can be delivered directly to the eye by ocular tissue injection such as periocular, conjunctival, subtenon, intracameral, intravitreal, intraocular, subretinal, subconjunctival, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or in the sclera (intrascleral) or within the eye. Intracanalicular injection may be into the venous collector channels draining Schlemm's canal or into Schlemm's canal.

For ophthalmic delivery, an antibody of the invention may be combined with ophthalmologically acceptable preservatives, co-solvents, surfactants, viscosity enhancers, penetration enhancers, buffers, sodium chloride, or water to form an aqueous, sterile ophthalmic suspension or solution. Topical ophthalmic products may be packaged, for example, in multidose form. Preservatives may thus be required to prevent microbial contamination during use. Suitable preservatives include: chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

In certain embodiments, compositions intended to be administered topically to the eye are formulated as eye drops or eye ointments, wherein the total amount of antibody will be about 0.1 to 10.0% (w/w). Preferably, the amount of TNFα antagonist, e.g., LME636, is about 5.0 to about 10.0% (w/w), most preferably about 6.0% (w/w).

Compositions of the invention in certain circumstances will be administered as solutions for topical administration. Aqueous solutions are generally preferred, based on ease of formulation, as well as a patient's ability to easily administer such compositions by means of instilling one to two drops of the solutions in the affected eyes. However, the compositions may also be suspensions, viscous or semi-viscous gels, or other types of solid or semi-solid compositions.

The therapeutically effective amount of an antibody present in the formulation is determined by taking into account the desired dose volumes and mode(s) of administration, for example. From about 1.0 mg/ml to about 100 mg/ml, preferably from about 5.0 mg/ml to about 80 mg/ml and most preferably from about 10.0 mg/ml to about 60 mg/ml is an exemplary antibody concentration in the formulation.

As a general proposition for systemic administration, the therapeutically effective amount of the TNFα antagonist, e.g., LME636, administered will be in the range of about 0.1 to about 100 mg/kg of patient body weight whether by one or more administrations, with the typical range of an antibody used being about 0.3 to about 20 mg/kg, more preferably about 0.3 to about 15 mg/kg, administered daily, for example. However, other dosage regimens may be useful. The progress of this therapy is easily monitored by conventional techniques.

Disclosed herein are methods of selectively treating a patient having DED, comprising either: a) selectively administering a therapeutically effective amount of a TNFα antagonist to the patient on the basis of the patient having a DED response marker wherein the DED response marker an rs1800693 response allele.

In some embodiments, the method further comprises the step of obtaining the biological sample from the patient, wherein the step of obtaining is performed prior to the step of assaying.

In some embodiments of the disclosed methods and uses, a DED response marker is detected by assaying the biological sample for a nucleic acid product of the DED response marker, a polypeptide product of the DED response marker, or an equivalent genetic marker of the DED response marker.

In some embodiments of the disclosed methods and uses, the DED response marker is detected by assaying the biological sample for a genomic sequence of the DED response marker.

In some embodiments of the disclosed methods and uses, the biological sample is selected from the group consisting of synovial fluid, blood, serum, feces, plasma, urine, tear, saliva, cerebrospinal fluid, a leukocyte sample and a tissue sample.

In some embodiments of the disclosed methods and uses, the DED response marker is detected by a technique selected from the group consisting of Northern blot analysis, polymerase chain reaction (PCR), reverse transcription-polymerase chain reaction (RT-PCR), TaqMan-based assays, direct sequencing, dynamic allele-specific hybridization, high-density oligonucleotide SNP arrays, restriction fragment length polymorphism (RFLP) assays, primer extension assays, oligonucleotide ligase assays, analysis of single strand conformation polymorphism, temperature gradient gel electrophoresis (TGGE), denaturing high performance liquid chromatography, high-resolution melting analysis, DNA mismatch-binding protein assays, SNPLex®, capillary electrophoresis, Southern Blot, immunoassays, immunohistochemistry, ELISA, flow cytometry, Western blot, HPLC, and mass spectrometry.

Kits

The invention also encompasses kits for detecting a DED response marker in a biological sample (a test sample) from a patient. Such kits can be used to predict if a patient having DED is likely to respond (or have a higher response) to treatment with a TNFα antagonist, e.g., TNFα binding molecule (e.g., TNFα antibody or antigen-binding portion thereof, e.g., LME636) or TNFα receptor binding molecule (e.g., TNFα antibody or antigen-binding portion thereof). For example, the kit can comprise a probe (e.g., an oligonucleotide, antibody, labeled compound or other agent) capable of detecting a DED response marker, products of those alleles and/or an equivalent genetic marker of those alleles in a biological sample. The kit may also comprise instructions for providing a prediction of the likelihood that the patient will respond to treatment with the TNFα antagonist.

Probes may specifically hybridize to genomic sequences, nucleic acid products, or polypeptide products. Exemplary probes are oligonucleotides or conjugated oligonucleotides that specifically hybridizes to the response alleles of Table 1 (e.g., from DNA, cDNA, mRNA, etc.); primer-extension oligonucleotides, allele-specific primers, a combination of allele-specific primers, allele-specific probes, and primer extension primers, etc. Optionally, the kit can contain a probe that targets an internal control allele, which can be any allele presented in the general population. Detection of an internal control allele is designed to assure the performance of the kit. The disclosed kits can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for use.

Such kits may also comprise a TNFα antagonist, e.g., TNFα binding molecule (e.g., TNFα antibody or antigen-binding portion thereof, e.g., LME636) or TNFα receptor binding molecule (e.g., TNFα antibody or antigen-binding portion thereof) (e.g., in liquid or lyophilized form) or a pharmaceutical composition comprising the TNFα antagonist (described supra). In this way, such kits are useful in the selective treatment of DED using a TNFα antagonist (e.g., LME636). Additionally, such kits may comprise means for administering the TNFα antagonist (e.g., a syringe and vial, a prefilled syringe, a prefilled pen) and instructions for use. These kits may contain additional therapeutic agents (described supra) for treating DED, e.g., for delivery in combination with the enclosed TNFα antagonist, e.g., LME636.

The phrase "means for administering" is used to indicate any available implement for systemically administering a drug top a patient, including, but not limited to, a pre-filled syringe, a vial and syringe, an injection pen, an autoinjector, an i.v. drip and bag, a pump, etc. With such items, a patient may self-administer the drug (i.e., administer the drug on their own behalf) or a physician may administer the drug.

General

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference. The following Examples are presented in order to more fully illustrate the preferred embodiments of the disclosure. These examples should in no way be construed as limiting the scope of the disclosed patient matter, as defined by the appended claims.

EXAMPLES

Example 1—CLME636X2202A Study: LME636 Improves Signs and Symptoms of Dry Eye Disease CLME636X2202A was a proof of concept (PoC) study to evaluate efficacy and safety of topical ocular treatment with LME636 in patients with severe dry eye disease (DED). The primary objective of the PoC study was to demonstrate the efficacy of topically administered LME636 over LME636 vehicle in reduction of ocular symptoms as determined by global ocular discomfort score at treatment day 29. The key secondary objective was to evaluate the percentage of patients with improvement in global ocular discomfort score >20 (responder analysis). DNA samples were collected from the patients with written informed consent, and an exploratory pharmacogenetics analysis was conducted to identify genetic factors that may influence the response to LME636 treatment. The pharmacogenetics analysis is described in Example 2.

During the treatment phase, 69 patients were randomized to receive LME636 and 65 to receive LME636 vehicle. 67 and 64 patients on LME636 and LME636 vehicle, respectively, completed the study and were part of the Per protocol analysis. Demographics and baseline characteristics were well balanced between the two groups including parameters (LME636 vs. LME636 vehicle): Mean age 61.7 vs. 58.8 years; Female patients 61 vs. 54; Mean global ocular discomfort at baseline 77.9 vs. 80.3.

For the primary efficacy endpoint, the change from baseline in global ocular discomfort score was (LME636 vs. LME636 vehicle): −7.9 [1.45 SE] vs. −3.6 [1.49 SE] at Day 29 (primary timepoint and per protocol analysis set) and −10.5 [1.74 SE] vs. −5.4 [1.77 SE] at Day 43 (exploratory timepoint with full analysis set). The 90% confidence interval for the difference in change from baseline at Day 29 was −7.7 to −0.8.

For LME636 vs. LME636 vehicle, the number of patients achieving an improvement from baseline in global ocular discomfort of 20 units or more at Day 29 were 12 (17.9%) vs. 3 (4.7%) with a p-value based on chi-square test and Wald interval of 0.018 (responder analysis).

In conclusion, the results met the prespecified criteria for the primary analysis and were further supported by the responder analysis. The improvements were sustained from Day 29 through Day 43.

Example 2: Materials and Method for Pharmacogenetic (PG) Analysis

Example 2.1: Samples and Processing

A total of 127 patient samples were collected. The patients who met all of the following criteria were included in the pharmacogenetics analysis:
  Provided written informed consent for pharmacogenetic study.
  DNA was successfully extracted and genotyped.
  Included in the analysis of overall clinical study.

Blood samples from consenting patients were collected at the individual trial sites and then shipped to Pharmaceutical Product Development (Wilmington, N.C. 28401). The genomic DNA of each patient was extracted from the blood by Covance (Indianapolis, Ind. 46214), and genotyping data was generated by Clinical Reference Laboratory (Lenexa, Kans. 66215) using TaqMan technology. Of the nine SNPs, eight were successfully developed, and one (rs115575857) failed to be developed due to complexity of local DNA sequence. Of the 127 DNA samples, 126 were successfully genotyped for the eight SNPs. One patient sample failed to be genotyped due to DNA quality issue. Two duplicated samples were included as quality control.

Several candidate genes and single nucleotide polymorphisms (SNPs) were selected for the PG analysis based on being in the drug target (TNF-α) or its receptor (TNFR1), or being genetic variants that were highly associated with Sjögren's syndrome (see Table 1).

TABLE 1

Candidate genes and SNPs

| Mechanism of action | | Sjögren's syndrome | |
| --- | --- | --- | --- |
| Gene | SNP | Gene | SNP |
| TNF-α | rs1800629 | HLA-DPB1 | rs4282438 |
| TNF-α | rs361525 | HLA-DQA1 | rs116232857 |
| TNF-α | rs1799724 | HLA-DRA | rs3135394 |
| TNFR1 | rs1800693 | HLA-DQB1 | rs115575857 |
| | | IRF5 | rs17339836 |

Example 2.2: Statistical Analysis

Primary Efficacy Endpoint

The primary efficacy endpoint was change from baseline in global ocular discomfort score at treatment day 29. The per-protocol set was used for the efficacy analysis.

To test genotype effect in patients treated with LME636: A mixed model repeated measures analysis was performed with terms of baseline global discomfort score, genotype, treatment day, genotype by treatment day interaction, age and race. Estimates of the difference in mean change from baseline in global discomfort between genotype groups and associated 90% confidence interval were presented.

To test interaction between genotype and treatment at treatment day 29: An ANCOVA model was used, and baseline global discomfort score, age and race were included as covariates. Estimates of the difference in mean change from baseline in global discomfort between genotype groups and associated 90% confidence interval were presented.

All statistical tests were 2-sided. A Bonferroni correction was applied to adjust for multiple testing. For any genetic effects attaining p≤0.1 after adjustment for multiple testing, a scatter plot or waterfall plot will be presented displaying individual patient data.

Key Secondary Efficacy Endpoint

The key secondary efficacy endpoint was percentage of patients with improvement in global ocular discomfort score >20 (determined as responder) from baseline to treatment day 29. The per-protocol set was used for the efficacy analysis.

Fisher's exact test was used. Only the genotypes that have been associated with the primary endpoint were analyzed. The percentage of patients with improvement in global ocular discomfort score >20 between genotype groups was presented.

Example 3: Results for PG Analysis

Example 3.1: Comparison for PG and Overall Study Populations

A total of 126 patient samples were successfully genotyped for 8 SNPs. The two duplicates that were introduced for quality control showed 100% concordance of the 8 SNPs genotypes. Of the 126 patients with genotype data, 88 entered the treatment. Of the 88 patients who had genotype data and entered the treatment, 86 were in the per protocol analysis set. In contrast, the overall study had 131 patients in the per protocol analysis set. Table 3 summarizes the demographic features, global ocular discomfort score at baseline, and the response rate by treatment in the PG population and overall study, respectively. The PG population looked similar to the overall study as determined by these variables, especially global ocular discomfort score at baseline.

TABLE 3

| | PG population | | Overall study | |
|---|---|---|---|---|
| Variable | LME636 (n = 43) | Vehicle (n = 43) | LME636 (n = 67) | Vehicle (n = 64) |
| Age, yrs | 62.18 (12.11) | 59.26 (14.01) | 61.61 (13.22) | 58.83 (14.60) |
| Race, % Caucasian | 74.42% | 79.07% | 74.63% | 79.69% |
| Gender, % female | 83.72% | 79.07% | 88.06% | 82.81% |
| Baseline GDS | 77.23 (13.53) | 80.84 (12.00) | 77.91 (13.89) | 80.33 (12.56) |
| Responder | 16.28% | 4.65% | 17.91% | 4.69% |

Comparison for PG and overall study population

Values are mean (SD).
Per protocol analysis set (PPS).

Example 3.2: Primary Efficacy Endpoint Analysis—Initial Association Test

Similar to the overall clinical study, a mixed model repeated measures analysis was used to test the association between the genotypes and change from baseline in global ocular discomfort score at treatment day 29. Among the 8 SNPs tested, only rs1800693 showed significant effect on the response to LME636 after Bonferroni correction ($p<0.0001$) (Table 4). The SNP rs1800629 showed a nominal significant association with the clinical endpoint ($p=0.0159$), but the significance disappeared after Bonferroni correction ($p=0.1272$).

TABLE 4

Initial screening for association between SNPs and response to LME636

| SNP | Genotype | LS Mean change | SE | (90% CI) | Nominal p-value |
|---|---|---|---|---|---|
| rs1799724 | CC (n = 32) | −3.50 | 3.58 | (−9.52, 2.53) | 0.3922 |
| (TNFα) | CT (n = 10) | −5.85 | 4.85 | (−13.99, 2.30) | |
| | TT (n = 1) | 0.09 | 12.6 | (−21.07, 21.25) | |
| rs1800629 | AG (n = 14) | −5.43 | 4.51 | (−13.00, 2.13) | 0.0159 |
| (TNFα) | GG (n = 29) | −3.64 | 3.47 | (−9.47, 2.20) | |
| rs361525 | AG (n = 5) | 1.32 | 6.31 | (−9.26, 11.893) | 0.5193 |
| (TNFα) | GG (n = 38) | −4.69 | 3.39 | (−10.39, 1.01) | |
| rs1800693 | CC (n = 4) | −29.48 | 6.52 | (−40.34, −18.61) | <0.0001* |
| (TNFR1) | CT (n = 25) | −0.09 | 3.52 | (−6.01, 5.83) | |
| | TT (n = 14) | −3.90 | 3.51 | (−9.79, 1.99) | |
| rs116232857 | AA (n = 11) | −1.61 | 4.30 | (−8.82, 5.60) | 0.9943 |
| (DQA1) | AG (n = 23) | −5.75 | 3.97 | (−12.43, 0.93) | |
| | GG (n = 9) | −4.57 | 4.98 | (−12.93, 3.78) | |
| rs3135394 | AA (n = 37) | −3.69 | 3.40 | (−9.40, 2.02) | 0.9649 |
| (DRA1) | AG (n = 6) | −5.37 | 6.41 | (−16.14, 5.39) | |
| rs4282438 | GG (n = 1) | N/A | N/A | N/A | 1.0000 |
| (DPB1) | GT (n = 2) | N/A | N/A | N/A | |
| | TT (n = 40) | N/A | N/A | N/A | |
| rs17339836 | CC (n = 37) | −4.60 | 3.42 | (−10.34, 1.15) | 0.9770 |
| (IRF5) | CT (n = 6) | −0.93 | 5.86 | (−10.75, 8.89) | |

Patients treated with LME636 for 29 day.
Per protocol analysis set (PPS).
Mixed model repeated measure to test the interaction between genotype and visit.
*Passed Bonferroni correction.

As shown in Table 5, the genotype effect of rs1800693 on symptomatic improvement only existed in the patients who were treated with LME636 but not in those who were treated with vehicle. The patients with CC genotype tended to have larger improvement than those with CT or TT genotypes.

TABLE 5

Association between rs1800693 and response to LME636

| Treatment | Genotype | LS Mean change | SE | (90% CI) | Nominal p-value |
|---|---|---|---|---|---|
| LME636 | CC (n = 4) | −29.48 | 6.52 | (−40.34, −18.61) | <0.0001 |
|  | CT (n = 25) | −0.09 | 3.52 | (−6.01, 5.83) |  |
|  | TT (n = 14) | −3.90 | 3.51 | (−9.79, 1.99) |  |

TABLE 5-continued

Association between rs1800693 and response to LME636

| Treatment | Genotype | LS Mean change | SE | (90% CI) | Nominal p-value |
|---|---|---|---|---|---|
| Vehicle | CC (n = 8) | −1.08 | 3.74 | (−7.32, 5.15) | 0.9863 |
|  | CT (n = 19) | −4.05 | 2.82 | (−8.77, 0.67) |  |
|  | TT (n = 16) | −4.03 | 2.80 | (−8.71, 0.65) |  |

Patients treated with LME636 or vehicle for 29 day.
Per protocol analysis set (PPS).
Mixed model repeated measure to test the interaction between genotype and visit.

Example 3.3: Primary Efficacy Endpoint Analysis—Interaction Between Treatment and Genotype Next, we tested if there was an interaction between treatment and genotypes using an analysis of covariance (ANCOVA) model. Similar to the initial mixed model analysis, only rs1800693 showed a significant interaction at treatment day 29 (p=0.0076) (Table 6). The interaction remained significant after Bonferroni correction (p=0.0608).

TABLE 6

Interaction between treatment and SNPs at treatment day 29

| SNP | Treatment | Genotype | LS Mean change | SE | (90% CI limits) | Nominal p-value |
|---|---|---|---|---|---|---|
| rs1799724 (TNFα) | LME636 | CC (n = 30) | −1.96 | 3.46 | (−7.73, 3.81) | 0.6211 |
|  |  | CT (n = 10) | −5.29 | 4.60 | (−12.96, 2.38) |  |
|  |  | TT (n = 1) | −0.43 | 11.07 | (−18.88, 18.02) |  |
|  | Vehicle | CC (n = 32) | −1.35 | 3.45 | (−7.10, 4.41) |  |
|  |  | CT (n = 9) | 0.43 | 4.78 | (−7.53, 8.39) |  |
|  |  | TT (n = 1) | 6.93 | 11.59 | (−12.39, 26.26) |  |
| rs1800629 (TNFα) | LME636 | AG (n = 13) | −1.55 | 4.33 | (−8.77, 5.68) | 0.5038 |
|  |  | GG (n = 28) | −2.59 | 3.54 | (−8.49, 3.30) |  |
|  | Vehicle | AA (n = 1) | 3.95 | 11.08 | (−14.52, 22.41) |  |
|  |  | AG (n = 8) | −2.66 | 4.44 | (−10.06, 4.73) |  |
|  |  | GG (n = 33) | 0.039 | 3.73 | (−6.18, 6.25) |  |
| rs361525 (TNFα) | LME636 | AG (n = 5) | 1.51 | 5.55 | (−7.73, 10.76) | 0.1522 |
|  |  | GG (n = 36) | −3.38 | 3.32 | (−8.91, 2.16) |  |
|  | Vehicle | AG (n = 4) | −5.96 | 5.98 | (−15.92, 3.99) |  |
|  |  | GG (n = 38) | −0.22 | 3.37 | (−5.83, 5.39) |  |
| rs1800693 (TNFR1) | LME636 | CC (n = 2) | −22.90 | 7.63 | (−35.61, −10.19) | 0.0076* |
|  |  | CT (n = 25) | −0.27 | 3.59 | (−6.25, 5.70) |  |
|  |  | TT (n = 14) | −4.10 | 3.59 | (−10.08, 1.88) |  |
|  | Vehicle | CC (n = 8) | 2.31 | 4.68 | (−5.49, 10.12) |  |
|  |  | CT (n = 18) | −2.26 | 3.84 | (−8.66, 4.15) |  |
|  |  | TT (n = 16) | −0.71 | 3.61 | (−6.72, 5.30) |  |
| rs116232857 (DQA1) | LME636 | AA (n = 10) | −1.25 | 4.19 | (−8.23, 5.73) | 0.6382 |
|  |  | AG (n = 22) | −4.02 | 3.93 | (−10.57, 2.53) |  |
|  |  | GG (n = 9) | −4.47 | 4.76 | (−12.41, 3.47) |  |
|  | Vehicle | AA (n = 15) | −2.86 | 4.25 | (−9.95, 4.22) |  |
|  |  | AG (n = 17) | −0.20 | 3.86 | (−6.64, 6.24) |  |
|  |  | GG (n = 10) | −2.01 | 4.56 | (−9.62, 5.59) |  |
| rs3135394 (DRA1) | LME636 | AA (n = 35) | −2.58 | 3.36 | (−8.18, 3.01) | 0.8775 |
|  |  | AG (n = 6) | −5.80 | 5.41 | (−14.82, 3.22) |  |
|  | Vehicle | AA (n = 36) | −0.93 | 3.41 | (−6.61, 4.74) |  |
|  |  | AG (n = 6) | −3.14 | 5.36 | (−12.06, 5.79) |  |
| rs4282438 (DPB1) | LME636 | GG (n = 1) | N/A | N/A | N/A | 0.7174 |
|  |  | GT (n = 2) | N/A | N/A | N/A |  |
|  |  | TT (n = 38) | N/A | N/A | N/A |  |
|  | Vehicle | GT (n = 2) | N/A | N/A | N/A |  |
|  |  | TT (n = 40) | N/A | N/A | N/A |  |
| rs17339836 (IRF5) | LME636 | CC (n = 35) | −3.52 | 3.28 | (−8.99, 1.95) | 0.0815 |
|  |  | CT (n = 6) | −1.08 | 5.25 | (−9.82, 7.67) |  |
|  | Vehicle | CC (n = 36) | −0.01 | 3.31 | (−5.53, 5.51) |  |
|  |  | CT (n = 6) | −8.77 | 5.24 | (−17.50, −0.04) |  |

ANCOVA model to test the interaction between treatment and genotype at day 29. Per protocol analysis set (PPS).
*Passed Bonferroni correction.

The interaction test was only for treatment day 29. However, there were missing values at individual treatment days. To improve the understanding of the interaction between treatment and rs1800693, we further tested the interaction from day 23 to day 28. As shown in Table 7, a similar trend of the interaction was observed from day 23 to 29.

TABLE 7

Interaction between treatment and rs1800693 from treatment day 23 to 29

| Treatment day | Treatment | Genotype | LS Mean change | SE | (90% CI limits) | p-value |
|---|---|---|---|---|---|---|
| Day 23 | LME636 | CC (n = 4) | −21.21 | 6.18 | (−31.51, −10.91) | 0.0023 |
| | | CT (n = 25) | 0.81 | 3.78 | (−5.49, 7.11) | |
| | | TT (n = 14) | −3.01 | 3.79 | (−9.32, 3.30) | |
| | Vehicle | CC (n = 8) | 2.27 | 4.93 | (−5.95, 10.48) | |
| | | CT (n = 18) | −1.96 | 4.04 | (−8.70, 4.78) | |
| | | TT (n = 14) | −4.27 | 3.86 | (−10.70, 2.16) | |
| Day 24 | LME636 | CC (n = 3) | −6.02 | 6.36 | (−16.62, 4.58) | 0.0190 |
| | | CT (n = 24) | 2.37 | 3.49 | (−3.45, 8.19) | |
| | | TT (n = 14) | −5.20 | 3.47 | (−10.99, 0.58) | |
| | Vehicle | CC (n = 7) | 1.60 | 4.73 | (−6.28, 9.48) | |
| | | CT (n = 18) | −4.96 | 3.74 | (−11.19, 1.27) | |
| | | TT (n = 16) | −0.32 | 3.49 | (−6.13, 5.49) | |
| Day 25 | LME636 | CC (n = 4) | −22.2 | 6.94 | (−33.76, −10.63) | 0.0030 |
| | | CT (n = 23) | 1.28 | 4.29 | (−5.87, 8.43) | |
| | | TT (n = 13) | −5.27 | 4.36 | (−12.53, 2.00) | |
| | Vehicle | CC (n = 7) | 2.93 | 5.78 | (−6.70, 12.56) | |
| | | CT (n = 18) | −3.69 | 4.54 | (−11.25, 3.88) | |
| | | TT (n = 16) | −3.88 | 4.26 | (−10.98, 3.23) | |
| Day 26 | LME636 | CC (n = 4) | −20.04 | 6.53 | (−30.93, −9.15) | 0.0031 |
| | | CT (n = 24) | 0.70 | 4.04 | (−6.04, 7.43) | |
| | | TT (n = 14) | −2.99 | 4.01 | (−9.67, 3.68) | |
| | Vehicle | CC (n = 8) | 3.00 | 5.25 | (−5.75, 11.75) | |
| | | CT (n = 16) | −3.50 | 4.33 | (−10.71, 3.72) | |
| | | TT (n = 15) | −5.53 | 4.15 | (−12.46, 1.40) | |
| Day 27 | LME636 | CC (n = 4) | −15.98 | 7.38 | (−28.27, −3.68) | 0.0679 |
| | | CT (n = 24) | 0.37 | 4.52 | (−7.17, 7.91) | |
| | | TT (n = 14) | −4.84 | 4.51 | (−12.36, 2.68) | |
| | Vehicle | CC (n = 8) | 2.58 | 5.88 | (−7.23, 12.38) | |
| | | CT (n = 16) | −2.08 | 4.90 | (−10.25, 6.09) | |
| | | TT (n = 16) | −2.69 | 4.53 | (−10.25, 4.86) | |
| Day 28 | LME636 | CC (n = 2) | −15.86 | 8.77 | (−30.48, −1.24) | 0.0881 |
| | | CT (n = 24) | 1.50 | 4.15 | (−5.42, 8.41) | |
| | | TT (n = 14) | −3.40 | 4.12 | (−10.28, 3.48) | |
| | Vehicle | CC (n = 7) | 2.33 | 5.64 | (−7.07, 11.73) | |
| | | CT (n = 18) | −2.23 | 4.44 | (−9.64, 5.18) | |
| | | TT (n = 14) | −2.89 | 4.22 | (−9.93, 4.16) | |
| Day 29 | LME636 | CC (n = 2) | −22.90 | 7.63 | (−35.61, −10.19) | 0.0076 |
| | | CT (n = 25) | −0.27 | 3.59 | (−6.25, 5.70) | |
| | | TT (n = 14) | −4.10 | 3.59 | (−10.08, 1.88) | |
| | Vehicle | CC (n = 8) | 2.31 | 4.68 | (−5.49, 10.12) | |
| | | CT (n = 18) | −2.26 | 3.84 | (−8.66, 4.15) | |
| | | TT (n = 16) | −0.71 | 3.61 | (−6.72, 5.30) | |

ANCOVA model to test interaction between treatment and genotype. Per protocol analysis set (PPS).

Example 3.4: Key Secondary Efficacy Endpoint Analysis

The secondary efficacy endpoint analysis focused on the response rate between genotype groups. Only rs1800693 was analyzed because it is the only SNP associated with the primary efficacy endpoint. As shown by the Fisher's exact test, the response rate was much greater in patients with CC genotype than those with CT or TT genotype (Table 8). The results are supportive to the primary efficacy endpoint analysis. However, the number of responders is small, so cautious interpretation is recommended.

TABLE 8

Response rate from treatment day 23 to 29

| Treatment day | Treatment | Genotype | Responder (%) | p-value* |
|---|---|---|---|---|
| Day 23 | LME636 | CC (n = 4) | 3 (75.00%) | 0.0137 |
| | | CT (n = 25) | 3 (12.00%) | |
| | | TT (n = 14) | 1 (7.14%) | |
| | Vehicle | CC (n = 8) | 0 (0.00%) | 0.6769 |
| | | CT (n = 18) | 2 (11.11%) | |
| | | TT (n = 14) | 0 (0.00%) | |
| Day 24 | LME636 | CC (n = 3) | 2 (66.67%) | 0.0414 |
| | | CT (n = 24) | 2 (8.33%) | |
| | | TT (n = 14) | 1 (7.14%) | |

TABLE 8-continued

Response rate from treatment day 23 to 29

| Treatment day | Treatment | Genotype | Responder (%) | p-value* |
|---|---|---|---|---|
| | Vehicle | CC (n = 7) | 0 (0.00%) | 0.6488 |
| | | CT (n = 18) | 2 (11.11%) | |
| | | TT (n = 16) | 0 (0.00%) | |
| Day 25 | LME636 | CC (n = 4) | 3 (75.00%) | 0.0160 |
| | | CT (n = 23) | 3 (13.04%) | |
| | | TT (n = 13) | 1 (7.69%) | |
| | Vehicle | CC (n = 7) | 0 (0.00%) | 0.6488 |
| | | CT (n = 18) | 2 (11.11%) | |
| | | TT (n = 16) | 0 (0.00%) | |
| Day 26 | LME636 | CC (n = 4) | 3 (75.00%) | 0.0149 |
| | | CT (n = 24) | 3 (12.50%) | |
| | | TT (n = 14) | 1 (7.14%) | |
| | Vehicle | CC (n = 8) | 0 (0.00%) | 0.5034 |
| | | CT (n = 16) | 2 (12.50%) | |
| | | TT (n = 15) | 0 (0.00%) | |
| Day 27 | LME636 | CC (n = 4) | 3 (75.00%) | 0.0149 |
| | | CT (n = 24) | 3 (12.50%) | |
| | | TT (n = 14) | 1 (7.14%) | |
| | Vehicle | CC (n = 8) | 0 (0.00%) | 0.3436 |
| | | CT (n = 16) | 2 (12.50%) | |
| | | TT (n = 16) | 0 (0.00%) | |
| Day 28 | LME636 | CC (n = 2) | 2 (100.00%) | 0.0211 |
| | | CT (n = 24) | 3 (12.50%) | |
| | | TT (n = 14) | 1 (7.14%) | |
| | Vehicle | CC (n = 7) | 0 (0.00%) | 0.6599 |
| | | CT (n = 18) | 2 (11.11%) | |
| | | TT (n = 14) | 0 (0.00%) | |
| Day 29 | LME636 | CC (n = 2) | 2 (100.00%) | 0.0199 |
| | | CT (n = 25) | 3 (12.00%) | |
| | | TT (n = 14) | 1 (7.14%) | |
| | Vehicle | CC (n = 8) | 0 (0.00%) | 0.6655 |
| | | CT (n = 18) | 2 (11.11%) | |
| | | TT (n = 16) | 0 (0.00%) | |

*Fisher's exact test.
Per protocol analysis set (PPS).

Example 3.5: Visualization of Individual Patient Data

There were 12 patients with CC genotype in this pharmacogenetics analysis. To visualize and compare the symptomatic changes between the treatments, the change from baseline in global ocular discomfort score of the 12 patients with CC genotype were plotted against the treatment days from baseline to day 43. As shown by FIG. 1, 3 of 4 patients treated with LME636 had large symptomatic improvements over time. In contrast, none of the eight (8) patients treated with vehicle showed consistently greater than 10 units of symptomatic improvement. The difference in symptomatic improvement between LME636 and vehicle at treatment day 29 was significant by an ANCOVA analysis (p<0.0001).

The change from baseline in global ocular discomfort score of all patients was further illustrated by waterfall plots to allow visualization of the symptomatic changes by treatment and genotype (FIGS. 2-5). Interestingly, only minimal vehicle response was seen in the patients with CC genotype, whereas vehicle responses of >10 occurred within CT and TT groups. The data suggested that the patients with CC genotype may have a type of dry eye disease that is less likely to be alleviated simply with vehicle.

Conclusion

This exploratory pharmacogenetic analysis used a candidate gene approach and focused on the genes relevant to mechanism of action of LME636 and the genes associated with Sjögren's syndrome. Due to small sample size, only 8 SNPs were included in the analysis to reduce the burden of adjustment for multiple testing. The three SNPs in the TNF-α gene were reported to associate with response to anti-TNF agents in patients with autoimmune diseases such as rheumatoid arthritis (Julia A, Fernandez-Nebro A, Blanco F, Ortiz A, Cañete J D, et al. (2016). A genome-wide association study identifies a new locus associated with the response to anti-TNF therapy in rheumatoid arthritis. Pharmacogenomics J. 16(2):147-50). The one SNP in the TNFR1 gene that was primarily associated with multiple sclerosis (MS) causes exon 6 skipping and results in production of soluble TNFR1 (sTNFR1) (De Jager P L, Jia X, Wang J, de Bakker P I, Ottoboni L, et al. (2009). Meta-analysis of genome scans and replication identify CD6, IRF8 and TNFRSF1A as new multiple sclerosis susceptibility loci. Nat Genet. 41(7):776-82; Gregory A P, Dendrou C A, Attfield K E, Haghikia A, Xifara D K, et al. (2012). TNF receptor 1 genetic risk mirrors outcome of anti-TNF therapy in multiple sclerosis. Nature. 23; 488(7412):508-11). To explore potential impact of the Sjögren's syndrome risk alleles on the response to LME636 in patients with DED, four SNPs strongly associated with Sjögren's syndrome were included in this analysis (Lessard C J, Li H, Adrianto I, Ice J A, Rasmussen A, Grundahl K M, et al. (2013). Variants at multiple loci implicated in both innate and adaptive immune responses are associated with Sjögren's syndrome. Nat Genet. 45(11):1284-92).

sTNFR1 is constitutively released from the cell membrane by TNF-α-converting enzyme, and its level increases in the course of various human diseases including Sjögren's syndrome, uveitis and glaucoma (Touchard E, Bloquel C, Bigey P, Kowalczuk L, Jonet L, et al. (2009). Local ocular immunomodulation resulting from electrotransfer of plasmid encoding soluble TNF receptors in the ciliary muscle. Gene Ther. 16(7):862-73; Sakimoto T, Yamada A, Sawa M. (2009). Release of soluble tumor necrosis factor receptor 1 from corneal epithelium by TNF-alpha-converting enzyme-dependent ectodomain shedding. Invest Ophthalmol Vis Sci. 50(10):4618-21; Sakimoto T, Ohnishi T, Ishimori A. (2014). Significance of ectodomain shedding of TNF receptor 1 in ocular surface. Invest Ophthalmol Vis Sci. 55(4):2419-23). In contrast, mutations that impair the process of sTNFR1 production cause periodic syndrome that is an auto-inflammatory disorder (Magnotti F, Vitale A, Rigante D, Lucherini O M, Cimaz R, et al. (2013). The most recent advances in pathophysiology and management of tumour necrosis factor receptor-associated periodic syndrome (TRAPS): personal experience and literature review. Clin Exp Rheumatol. 31(3 Suppl 77):141-9). Therefore, an imbalance of sTNFR1 production may contribute to pathogenesis of human diseases. Some mechanistic studies suggested that sTNFR1 may act as physiological attenuators of TNF-α activity, or may function as a buffer system to enhance the effect of TNF-α (Aderka D, Engelmann H, Maor Y, Brakebusch C, Wallach D. (1992). Stabilization of the bioactivity of tumor necrosis factor by its soluble receptors. J Exp Med. 175(2):323-9; Gregory A P, Dendrou C A, Attfield K E, Haghikia A, Xifara D K, et al. (2012). TNF receptor 1 genetic risk mirrors outcome of anti-TNF therapy in multiple sclerosis. Nature. 23; 488(7412):508-11). rs1800693 is considered as a novel mechanism of sTNFR1 production. A recent study demonstrated that the rs1800693 CC genotype was correlated with increased signaling to TNF-α and that this altered signaling may be due to altered localization of sTNFR1 within the cells (Housley W J, Fernandez S D, Vera K, Murikinati S R, Grutzendler J, et al. (2015). Genetic variants associated with autoimmunity drive NFκB signaling and responses to inflammatory stimuli. Sci Transl Med. 10; 7(291):291ra93).

The prevalence of CC is 19.9% and 12.7% in Caucasian and African, respectively, as reported in 1000 human genome database. In contract, the prevalence of CC is 11.5% (11/96) and 12.7% (2/19) in Caucasian and African, respectively, in the LME636X2202 study. No genome-wide genetic association study for dry eye disease has been reported in literature. It is not clear if rs1800693 has any impact on the risk for dry-eye disease.

We have identified, inter alia, a particular genetic variant that is predictive of response to TNFα antagonism, e.g., a TNFα antibody, e.g., LME636, in DED. The findings disclosed herein could not have been predicted based solely on the fact that a certain SNP may be associated with an increased likelihood of a patient developing DED. The findings disclosed herein could not have been predicted based solely on the particular genes in which the SNPs were studied. Indeed, of the eight SNPs tested, four were known to be associated with the TNFα pathway and four were known to be associated with Sjögren's syndrome, but only rs1800693 located in the TNFR1 gene showed a significant effect on the response to LME636 treatment. The patients with CC genotype tended to have much greater improvement on the symptoms than those with CT or TT genotype. As such, one cannot predict how a patient will respond to a drug based solely on whether that patient carries an allele associated with a particular disease state or whether the patient carries a SNP in a particular gene.

We conclude that the predictive methods and personalized therapies disclosed herein are useful to maximize the benefit and minimize the risk of TNFα antagonism in patients having DED by identifying those patients likely to respond prior to treatment with a TNFα antagonist, such as LME636.

What is claimed is:

1. A method of selectively treating a patient having dry eye disease (DED), comprising:
   a) determining or having determined that the patient has a CC genotype at rs 1800693:
   b) diagnosing the patient as more likely to respond to a DED treatment comprising a TNFα antagonist compared to a subject with a CT or a TT genotype; and
   c) administering the TNFα antagonist to the diagnosed subject, wherein the TNFα antagonist is the TNFα antibody LME636, comprising a variable heave chain (VH) comprising SEQ ID NO: 8, and a variable light chain (VL) comprising SEQ ID NO: 7.

2. The method according to claim 1, wherein the rs1800693 CC response allele is identified as a nucleic acid product in a biological sample.

3. The method according to claim 2, wherein the nucleic acid is a genomic sequence in the biological sample.

4. The method according to claim 3, wherein the biological sample is selected from the group consisting of synovial fluid, blood, serum, feces, plasma, urine, tears, saliva, cerebrospinal fluid, a leukocyte sample and a tissue sample.

* * * * *